(12) United States Patent
Kumar et al.

(10) Patent No.: US 12,023,462 B2
(45) Date of Patent: Jul. 2, 2024

(54) FLUID CONNECTOR SYSTEM

(71) Applicant: CAREFUSION 303, INC., San Diego, CA (US)

(72) Inventors: Manish Kumar, Karnataka (IN); Praveen Nalawade, Karnataka (IN); Karthik MR, Karnataka (IN); Balaji K, Tamilnadu (IN)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 17/956,506

(22) Filed: Sep. 29, 2022

(65) Prior Publication Data
US 2024/0108874 A1 Apr. 4, 2024

(51) Int. Cl.
*A61M 39/26* (2006.01)
*A61M 39/10* (2006.01)
(Continued)

(52) U.S. Cl.
CPC ............ *A61M 39/26* (2013.01); *A61M 39/10* (2013.01); *F16L 37/30* (2013.01); *A61M 2039/1061* (2013.01); *A61M 2039/2426* (2013.01); *A61M 2039/2433* (2013.01); *A61M 2039/246* (2013.01)

(58) Field of Classification Search
CPC .... A61M 2039/2426; A61M 2039/246; A61M 2039/2446; A61M 2039/2433; A61M 2039/1061; A61M 39/10; A61M 39/26; F16L 37/30; F16L 37/32; F16L 29/04; F16L 55/1007; F16L 55/1015
See application file for complete search history.

(56) References Cited

U.S. PATENT DOCUMENTS

| | | | | |
|---|---|---|---|---|
| 4,610,469 A | * | 9/1986 | Wolff-Mooij | A61M 39/26 604/905 |
| 4,804,015 A | * | 2/1989 | Albinsson | F16L 37/30 251/342 |

(Continued)

FOREIGN PATENT DOCUMENTS

| | | | | |
|---|---|---|---|---|
| JP | 2004209278 A | * | 7/2004 | ............ A61M 39/24 |
| WO | WO-2006122406 A1 | * | 11/2006 | ............ A61M 39/26 |

OTHER PUBLICATIONS

International Search Report and Written Opinion for Application No. PCT/US2023/030166, dated Nov. 6, 2023, 14 pages.

*Primary Examiner* — David Colon-Morales
(74) *Attorney, Agent, or Firm* — Morgan, Lewis & Bockius LLP

(57) ABSTRACT

Fluid connector systems including first and second connector portions couplable together to form a fluid pathway therethrough, and can resist fluid flow through the connector when the connector portions are separated from each other. A connector portion can include a connector housing, a luer portion, and a deformable valve member. The deformable valve member is disposed within the connector housing and includes a spherical portion extending partially through a valve opening of the connector housing. The spherical portion defines a slit, and the deformable valve member is configured to selectively prevent fluid flow from the housing volume through the valve opening and to deform to expand the slit and permit fluid flow from the housing volume through the valve opening.

14 Claims, 28 Drawing Sheets

(51) Int. Cl.
*A61M 39/24* (2006.01)
*F16L 37/30* (2006.01)

(56) References Cited

U.S. PATENT DOCUMENTS

| | | | |
|---|---|---|---|
| 5,520,665 A | 5/1996 | Fleetwood | |
| 5,820,614 A * | 10/1998 | Erskine | F16L 55/1007 |
| | | | 604/905 |
| 6,808,161 B1 * | 10/2004 | Hishikawa | F16L 29/005 |
| | | | 604/167.04 |
| 6,811,139 B2 * | 11/2004 | Hishikawa | A61M 39/26 |
| | | | 604/905 |
| 6,851,448 B2 * | 2/2005 | Fujii | F16K 15/147 |
| | | | 137/515 |
| 6,964,406 B2 * | 11/2005 | Doyle | F16L 29/04 |
| | | | 251/149.6 |
| 7,530,546 B2 * | 5/2009 | Ryan | A61M 39/26 |
| | | | 604/905 |
| 7,841,581 B2 * | 11/2010 | Thorne, Jr. | A61M 39/26 |
| | | | 251/149.6 |
| 8,025,646 B2 * | 9/2011 | Fukai | A61M 39/045 |
| | | | 604/256 |
| 8,377,039 B2 * | 2/2013 | Utterberg | A61M 39/26 |
| | | | 604/533 |
| 8,899,267 B2 * | 12/2014 | Diodati | A61M 39/18 |
| | | | 137/614.04 |
| 8,974,425 B2 * | 3/2015 | Tachizaki | F16L 37/30 |
| | | | 604/905 |
| 9,933,094 B2 * | 4/2018 | Fangrow | A61M 39/26 |
| 10,137,291 B2 * | 11/2018 | Guala | A61M 39/20 |
| 10,179,231 B2 * | 1/2019 | Nelson | A61M 39/26 |
| 10,286,203 B2 * | 5/2019 | Gagliardoni | A61M 39/26 |
| 10,315,025 B2 * | 6/2019 | Phillips | A61M 39/26 |
| 10,625,068 B2 * | 4/2020 | Leuthardt | A61M 39/10 |
| 10,625,070 B2 * | 4/2020 | Schlitt | A61M 39/26 |
| 10,655,768 B2 * | 5/2020 | Jones | A61M 39/24 |
| 10,751,523 B2 * | 8/2020 | Rogier | F16K 3/28 |
| 10,864,362 B2 * | 12/2020 | Jones | A61M 5/16813 |
| 10,881,847 B2 * | 1/2021 | Lynn | A61M 39/10 |
| 11,135,417 B2 * | 10/2021 | Yoshioka | A61M 39/24 |
| 11,235,136 B2 * | 2/2022 | Rogier | A61M 39/26 |
| 11,679,246 B2 * | 6/2023 | Lynn | A61M 39/10 |
| | | | 604/256 |
| 2008/0128646 A1 * | 6/2008 | Clawson | F16K 27/08 |
| | | | 215/329 |
| 2010/0318039 A1 | 12/2010 | Hall et al. | |

* cited by examiner

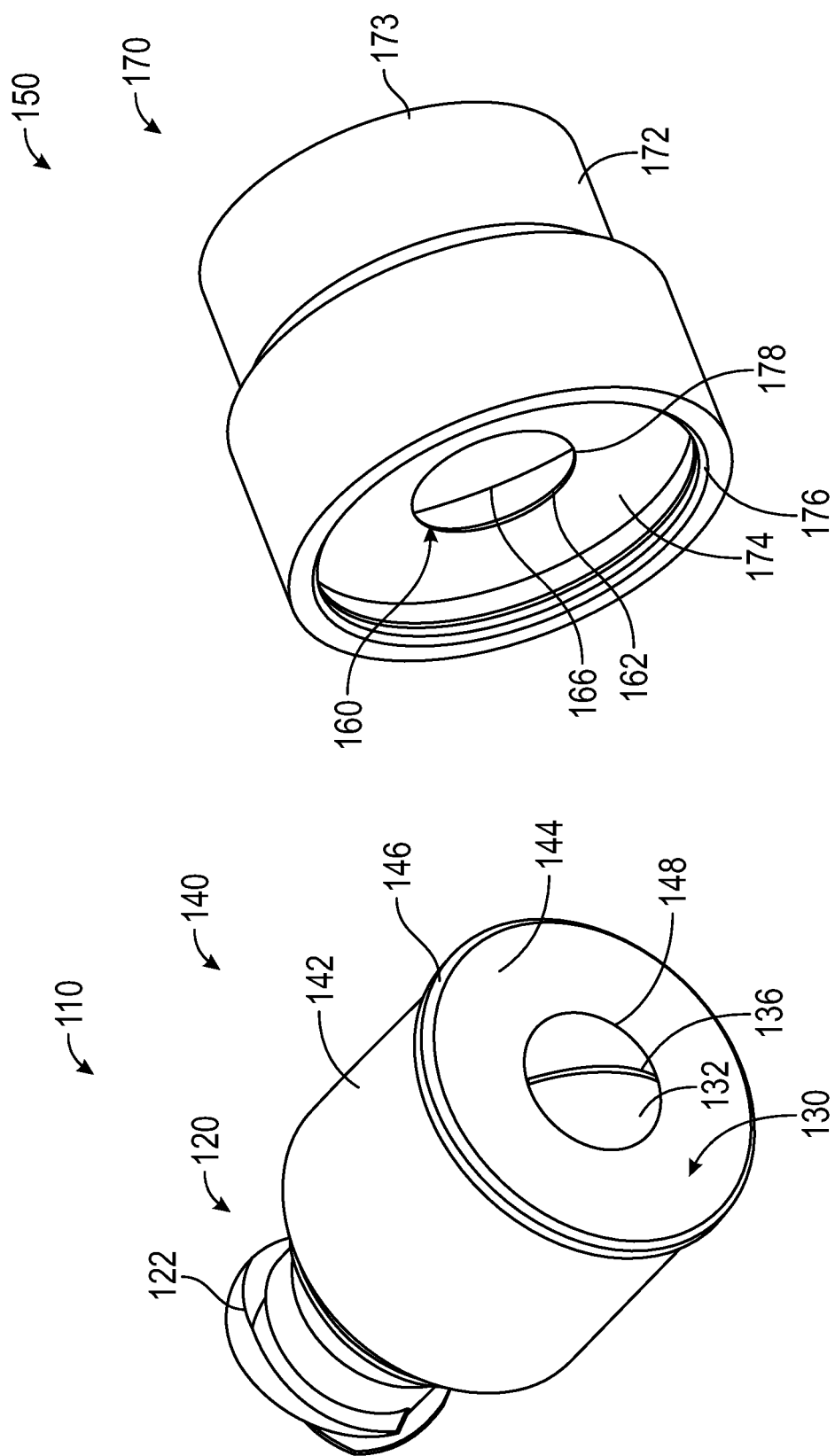

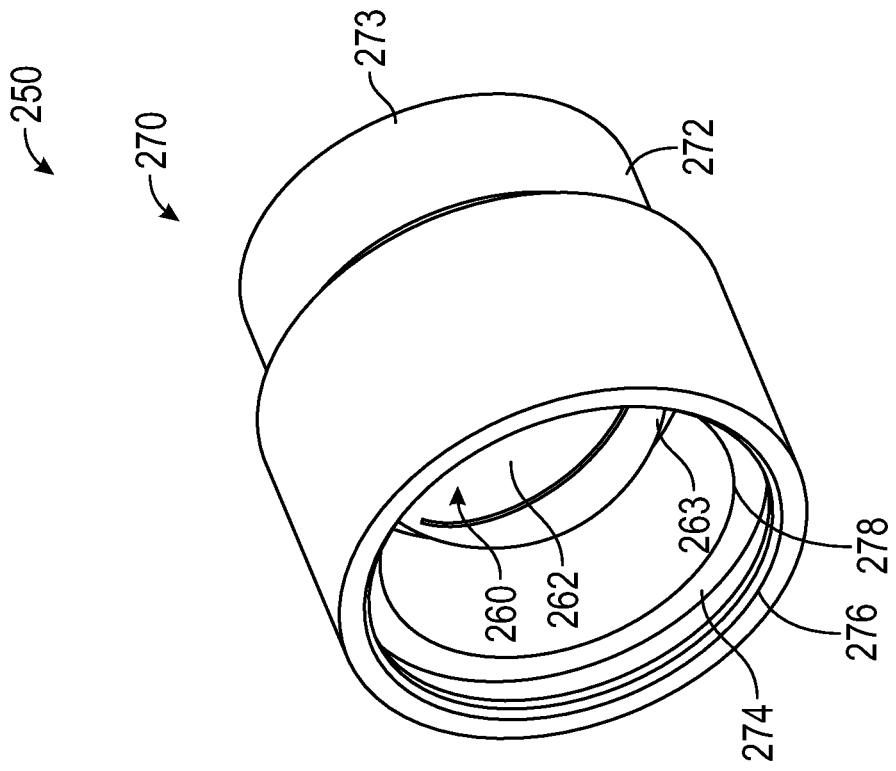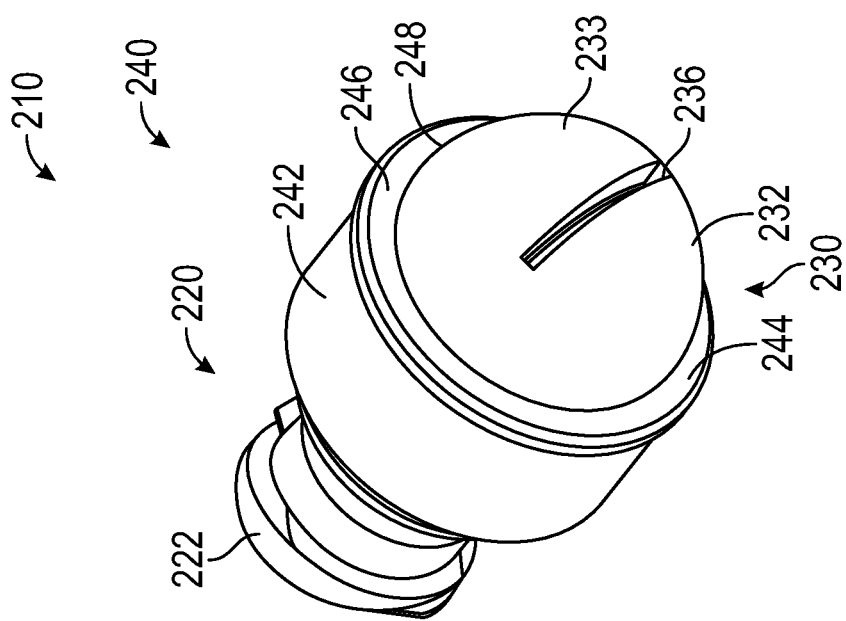
FIG. 8

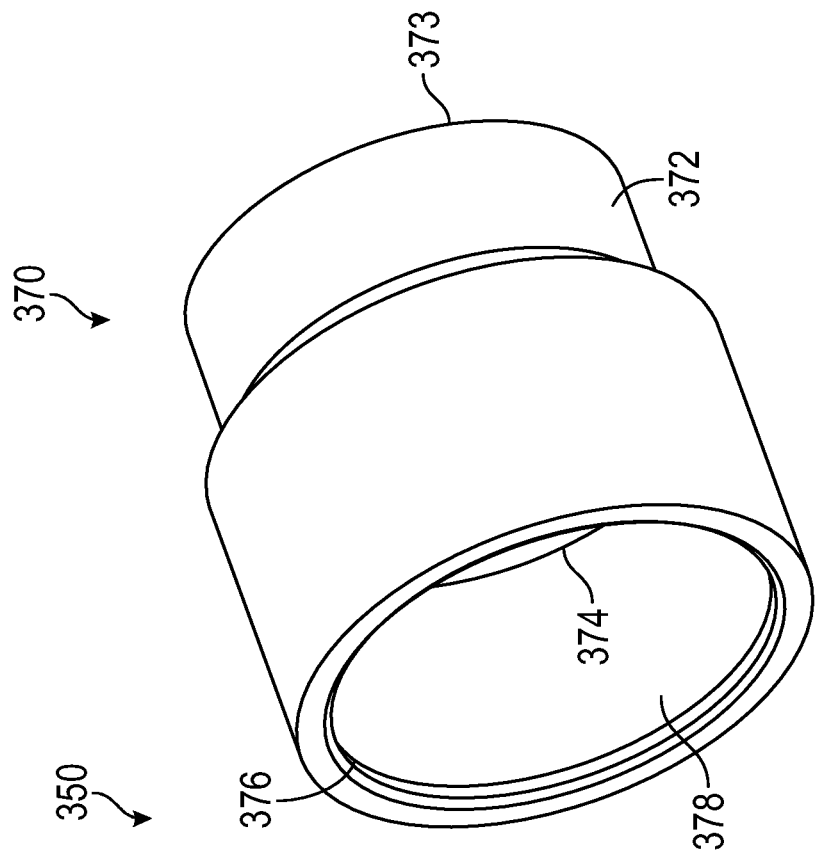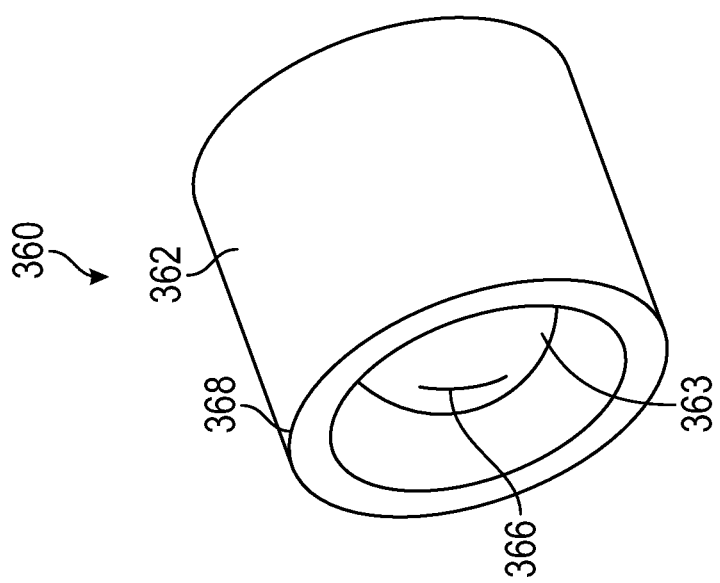
FIG. 16

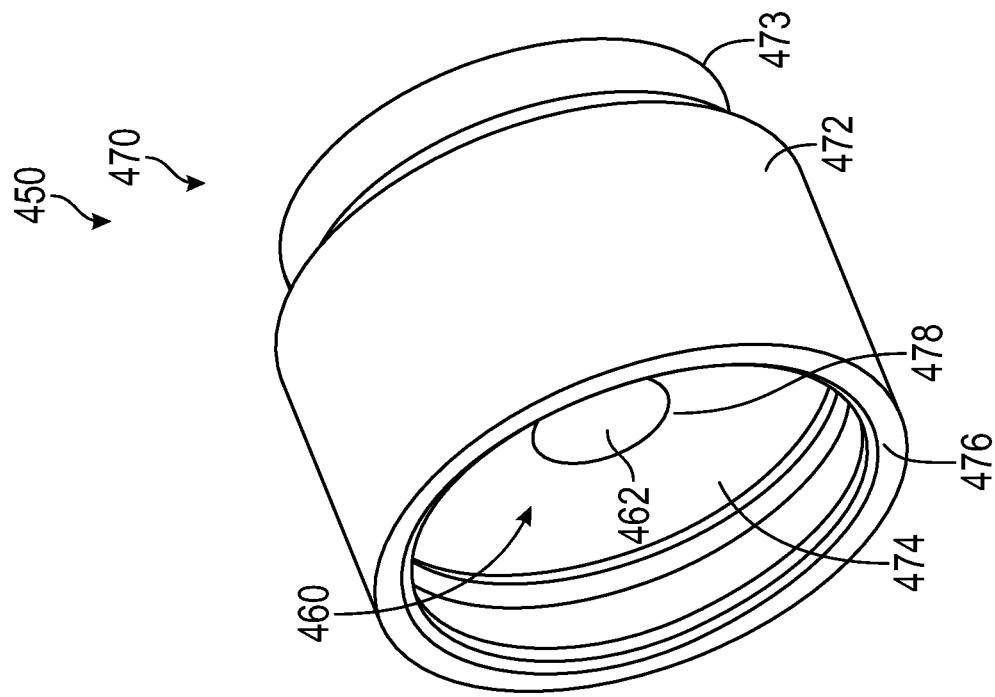
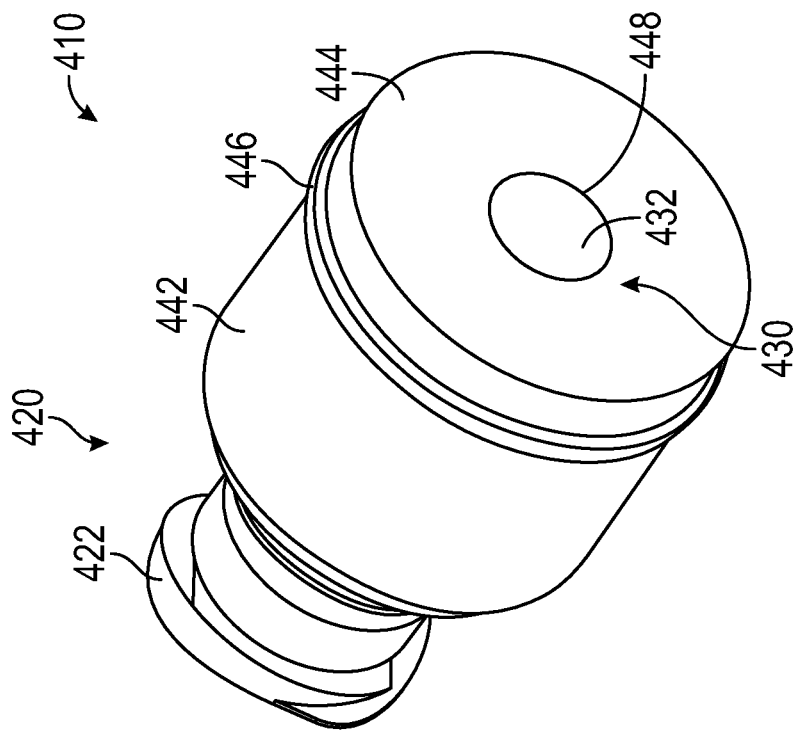
FIG. 18

FLUID CONNECTOR SYSTEM

BACKGROUND

The present disclosure relates generally to medical fluid connectors and, more particularly, to fluid connector systems having valve assemblies that can be coupled together to form a fluid pathway.

Medical connections are widely used in fluid delivery systems such as those used in connection with intravenous (IV) fluid lines, blood access, hemodialysis, peritoneal dialysis, enteral feeding, drug vial access, and other procedures.

In some instances, the medical connection can become dislodged or disconnected in an unintended manner. For example, medical tubing of an IV set that is coupled to a catheter can become dislodged when an unintended or unexpected forces is exerted upon the catheter, which may exceed the design limitations of the catheter securement method. An unintended or unexpected force can be applied to the tubing and/or catheter when the patient moves or rolls over within a bed, or when the tubing or another portion of an intravenous set become caught on a portion of the bed, such as the railing, or when a patient is panicking, disoriented, or fidgeting to such an extent that the medical tubing is unintentionally or intentionally pulled away from the patient or away from the medical equipment coupled to the tubing.

SUMMARY

In accordance with at least some embodiments disclosed herein is the realization that unintended dislodgement or disconnection of a medical connection, such as a medical fluid line, can result in injury to a patient or a caregiver, such as by depriving the patient of a medicament, increasing the potential for infection to the patient, and exposing the caregiver to harmful medicaments.

Accordingly, aspects of the present disclosure provide a connector comprising: a first connector portion comprising: a connector housing comprising a connector body defining a housing volume, a luer opening and a valve opening, wherein the housing volume is in fluid communication with the luer opening and the valve opening; a luer portion comprising a luer end and a housing end, the luer portion defining a lumen extending between the luer end and the housing end, wherein the housing end of the luer portion extends through the luer opening of the connector body to couple the luer portion to the connector housing and the lumen is in fluid communication with the housing volume; and a deformable valve member disposed within the housing volume and comprising a spherical portion extending partially through the valve opening, wherein the spherical portion defines a slit, and the deformable valve member is configured to selectively prevent fluid flow from the housing volume through the valve opening and to deform to expand the slit and permit fluid flow from the housing volume through the valve opening.

In some instances, the present disclosure provides a connector comprising a first connector portion comprising: a connector housing comprising a connector body defining a housing volume, a luer opening and a valve opening, wherein the housing volume is in fluid communication with the luer opening and the valve opening; a luer portion comprising a luer end and a housing end, the luer portion defining a lumen extending between the luer end and the housing end, wherein the housing end of the luer portion extends through the luer opening of the connector body to couple the luer portion to the connector housing and the lumen is in fluid communication with the housing volume; and a spherical valve member disposed within the housing volume, wherein the spherical valve member is configured to selectively obstruct the valve opening to prevent fluid flow from the housing volume through the valve opening and to displace away from the valve opening and permit fluid flow from the housing volume through the valve opening.

In some instances, the present disclosure provides a connector comprising a connector housing comprising a connector body defining a housing volume, a luer opening and a valve opening, wherein the housing volume is in fluid communication with the luer opening and the valve opening; a luer portion comprising a luer end and a housing end, the luer portion defining a lumen extending between the luer end and the housing end, wherein the housing end of the luer portion extends through the luer opening of the connector body to couple the luer portion to the connector housing and the lumen is in fluid communication with the housing volume; a spherical valve member disposed within the housing volume; and a movable flange movably coupled to the connector housing, wherein the movable flange comprises a protrusion defining a flange channel, wherein the spherical valve member is configured to selectively prevent flow through the housing volume when the protrusion of the movable flange and the spherical valve member are spaced apart and to displace the spherical valve member away from the valve opening and permit fluid flow between the valve opening and the flange channel when the spherical valve member and the protrusion of the flange are in contact.

Accordingly, the present application addresses several operational challenges encountered in prior fluid connections and provides numerous improvements that enable the user to increase safety and efficacy, while more easily and precisely providing fluid connections.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIG. 3 illustrates a perspective view of the connector portions of the fluid connector of FIG. 2, in accordance with aspects of the present disclosure.

FIG. 8 illustrates a perspective view of the connector portions of the fluid connector of FIG. 7, in accordance with aspects of the present disclosure.

FIG. 16 is an exploded perspective view of a second connector portion of the fluid connector of FIG. 12, in accordance with aspects of the present disclosure.

FIG. 18 illustrates a perspective view of the connector portions of the fluid connector of FIG. 17, in accordance with aspects of the present disclosure.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although particular embodiments of the present disclosure may be disclosed or shown in the context of an IV set, such embodiments can be used in other fluid conveyance systems. Furthermore, various applications of such embodiments and modifications thereto, which may occur to those who are skilled in the art, are also encompassed by the general concepts described herein.

In accordance with some embodiments, the present application discloses various features and advantages of a fluid connector system. The fluid connector system can provide for efficient and safe maintenance of fluid connections, such as the connections used for transferring medical fluids toward or away from a patient. The fluid connector system can maintain a fluid pathway by resisting unintended disconnection when a pulling or tension force is applied to the fluid connector system, such as when a patient moves or when the medical tubing is pulled away from the patient.

The fluid connector system can also prevent injury to a patient or a caregiver by permitting disconnection or separation between portions of the connector system when a pulling or tension force exceeds a threshold. The fluid connector system can also prevent injury to a patient or a caregiver by obstructing the fluid pathway when disconnection or separation between portions of the connector system occurs. Further, the fluid connector system can provide for efficient and safe reestablishment of the fluid pathway, by permitting reassembly of portions of the system after a disconnection or separation occurs. Advantageously, the fluid connectors described herein can prevent blood loss, IV fluid loss, infection, and/or delays in medication delivery. In some applications, the design of the fluid connectors can facilitate effective cleaning and sanitization of the components. Further, in some applications, the connectors described herein can be manufactured for relatively low cost.

Figure 1:
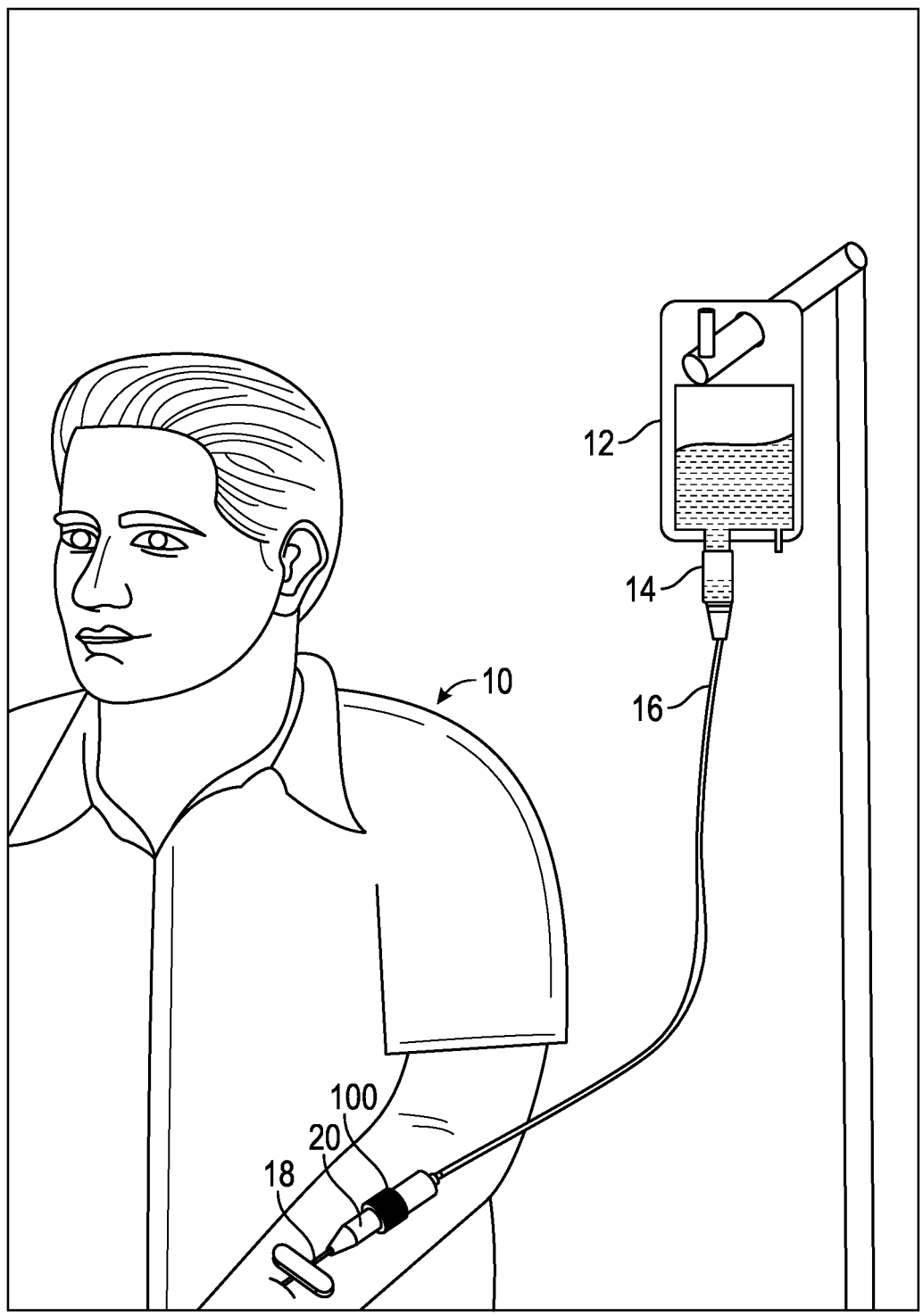
FIG. 1 illustrates a fluid connector in use with an IV set coupled to a patient, in accordance with aspects of the present disclosure.

Referring now to the figures, FIG. 1 illustrates an example of a fluid connector 100 in use in accordance with aspects of the present disclosure. The connector system 100 is coupled with tubing of an IV set, which is being used to direct a fluid to a patient 10. The IV set can include a medicament bag 12, a drip chamber 14, tubing 16, and an IV catheter 18.

The connector system 100 fluidly connects the tubing 16 to the IV catheter 18. Although the connector system 100 is illustrated being coupled along a fluid pathway of an IV set, between a medicament bag 12 and a patient 10, it should be understood that the connector system 100 can be connected within other fluid pathways, such as between a patient and a IV pump or between a patient and a dialysis machine. The connector system 100 can also be connected along another portion of a fluid pathway. For example, the connector system 100 can be connected along a proximal portion of the fluid pathway, such as being connected between the tubing 16 and the medicament bag 12 or other fluid therapy device. In another example, any of the first and second portions of the fluid connector 100 can be directly coupled to another fluid delivery devices, such as the catheter or a medicament bag.

Figure 2:
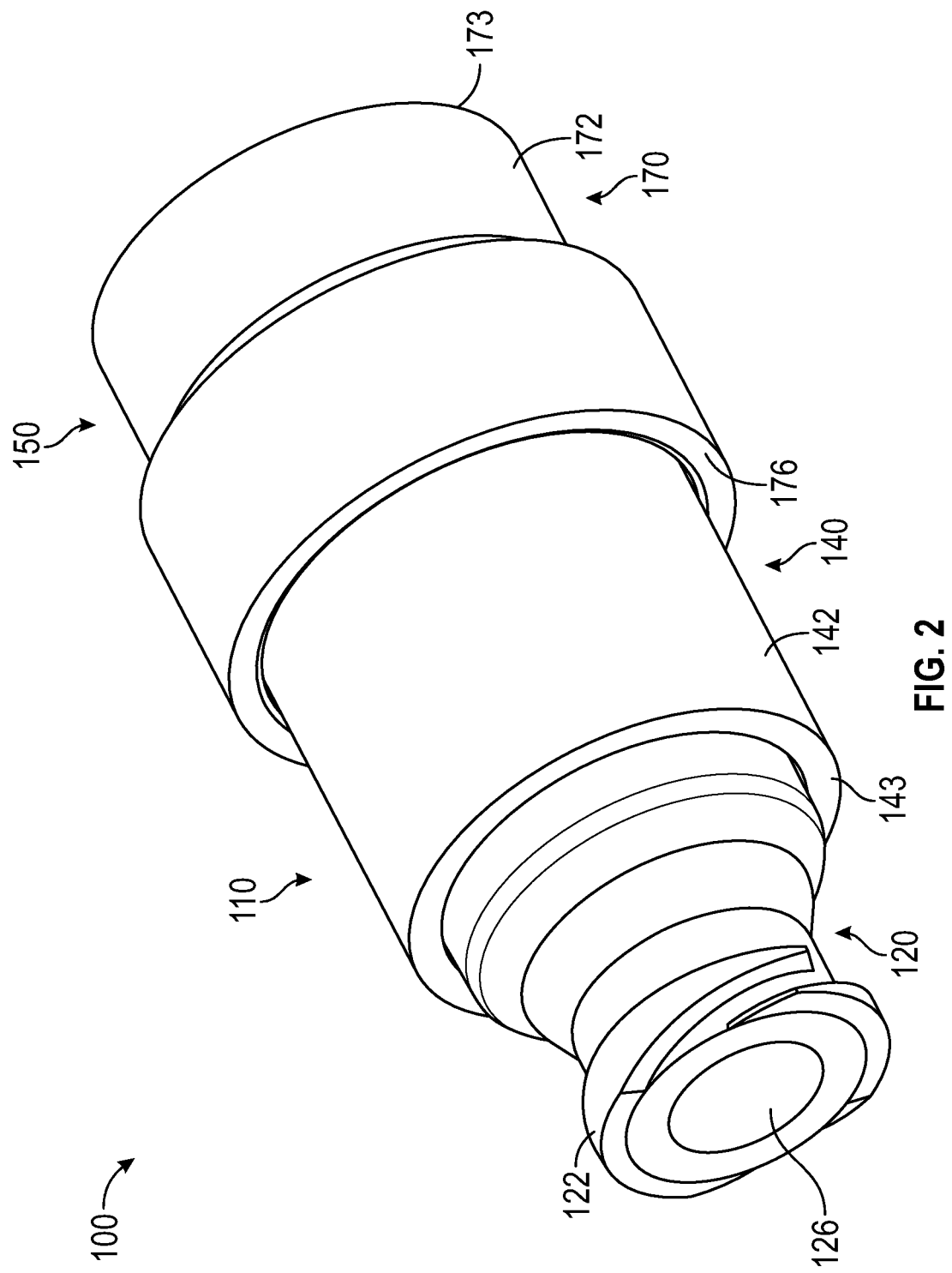
FIG. 2 illustrates a perspective view of a fluid connector, in accordance with aspects of the present disclosure.

FIG. 2 illustrates a perspective view of a fluid connector 100, in accordance with aspects of the present disclosure. With reference to FIG. 2, the fluid connector 100 provides a fluid pathway to a patient while allowing for a "fusible link" or quick disconnect, allowing for a controlled disconnection of the fluid connector 100 if excess force is applied. As described herein, the fluid connector 100 can allow for controlled disconnection at a predetermined level of force to prevent a catheter from being inadvertently removed from the patient.

Figure 4A:
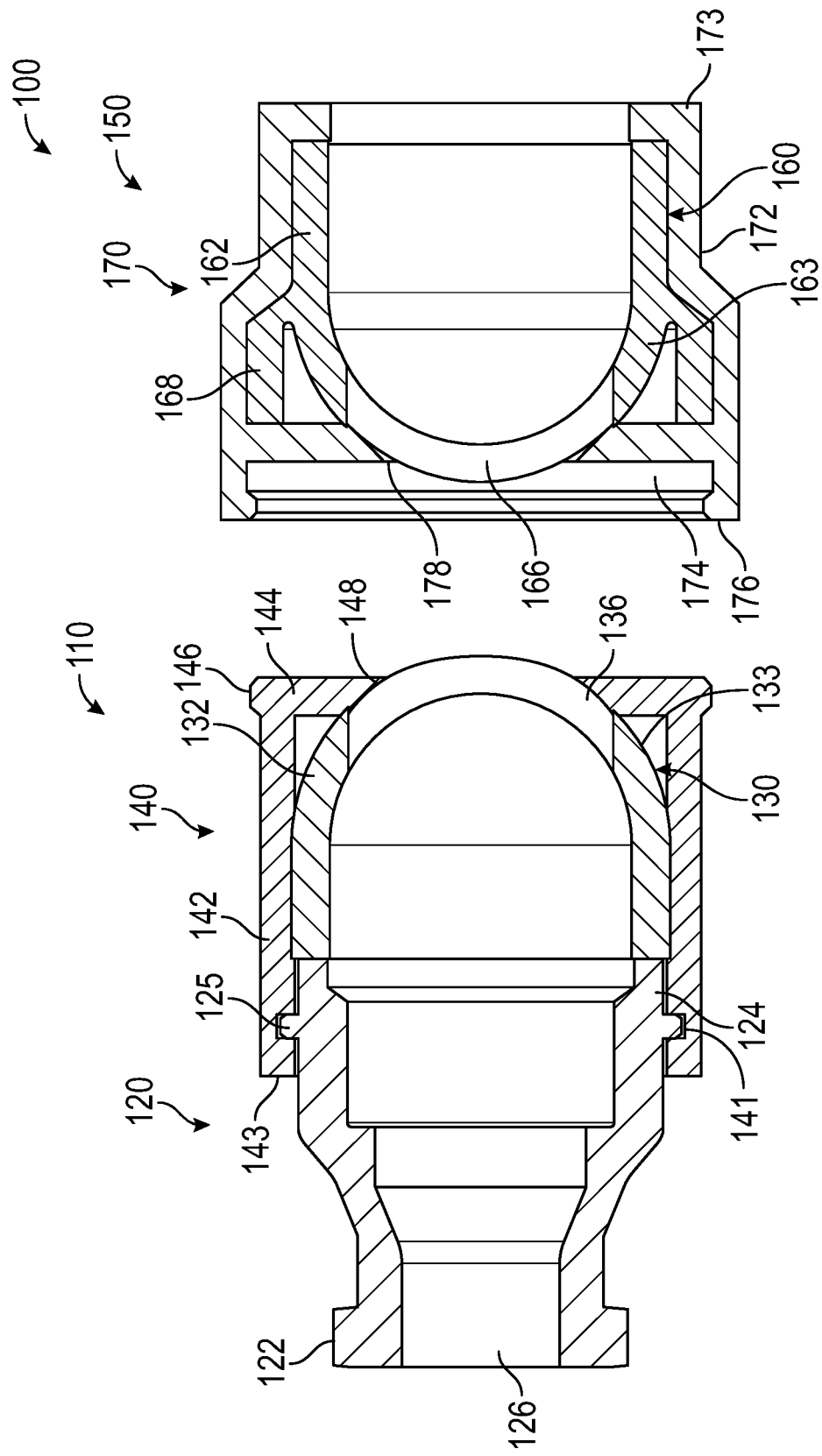
FIG. 4A illustrates a cross-sectional view of a separated fluid connector of FIG. 2, in accordance with aspects of the present disclosure.
Figure 4B:
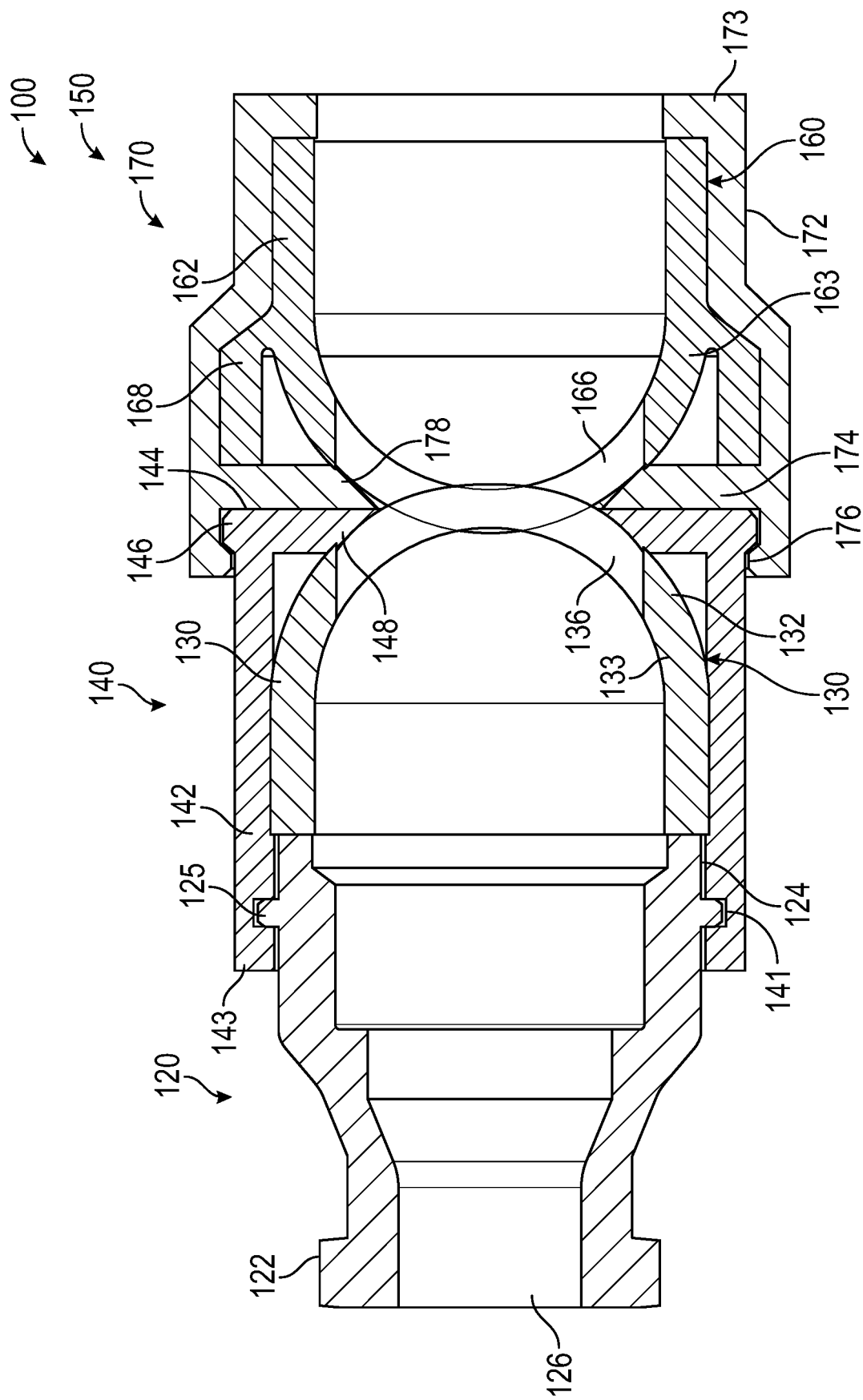
FIG. 4B illustrates a cross-sectional view of the connected fluid connector of FIG. 2, in accordance with aspects of the present disclosure.

FIG. 3 illustrates a perspective view of the connector portions 110, 150 of the fluid connector 100 of FIG. 2, in accordance with aspects of the present disclosure. FIG. 4A illustrates a cross-sectional view of a separated fluid connector 100 of FIG. 2, in accordance with aspects of the present disclosure. FIG. 4B illustrates a cross-sectional view of the connected fluid connector 100 of FIG. 2, in accordance with aspects of the present disclosure. With reference to FIGS. 2-4B, the fluid connector 100 provides a flow path or fluid pathway from one end of the fluid connector 100 to the opposite end of the fluid connector 100. As illustrated, the fluid connector 100 includes a first connector portion 110 and a second connector portion 150 that are coupled together to form a fluid pathway.

Figure 5:
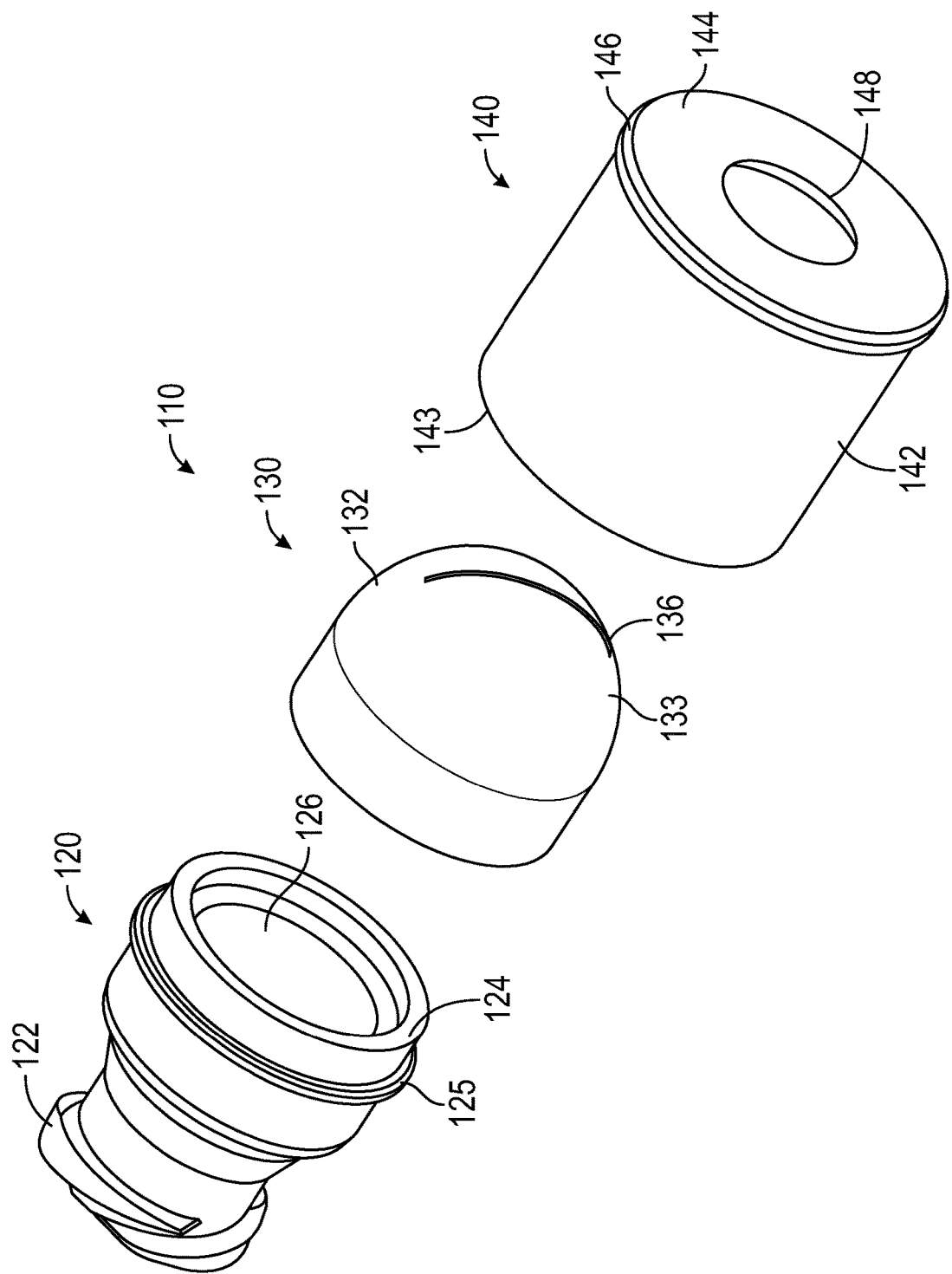
FIG. 5 is an exploded perspective view of a first connector portion of the fluid connector of FIG. 2, in accordance with aspects of the present disclosure.

FIG. 5 is an exploded perspective view of a first connector portion 110 of the fluid connector 100 of FIG. 2, in accordance with aspects of the present disclosure. With reference to FIGS. 2-5, the first connector portion 110 permits fluid flow to and from the patient or any other portion of the IV set. In the depicted example, the first connector portion 110 includes a luer portion 120 to allow the first connector portion 110 to be connected to a mating luer connector. As illustrated, a mating luer connector can be attached to the luer threads 122. Fluid can pass to and from the fluid connector 100 through the mating luer connector via a lumen 126 defined in the luer portion 120. In the depicted example, the luer portion 120 can be coupled to the other portions of the first connector portion 110. In some embodiments, a housing end 124 of the luer portion 120 can be coupled to a luer end 143 of a connector housing 140. Optionally, the housing end 124 of the luer portion 120 can define a ridge 125. As illustrated, the ridge 125 can engage with a groove 141 defined at or near the luer end 143 of the connector housing 140 to define a snap fitting or snap joint between the luer portion 120 and the connector housing 140 and selectively couple the luer portion 120 and the connector housing 140.

Figure 6:
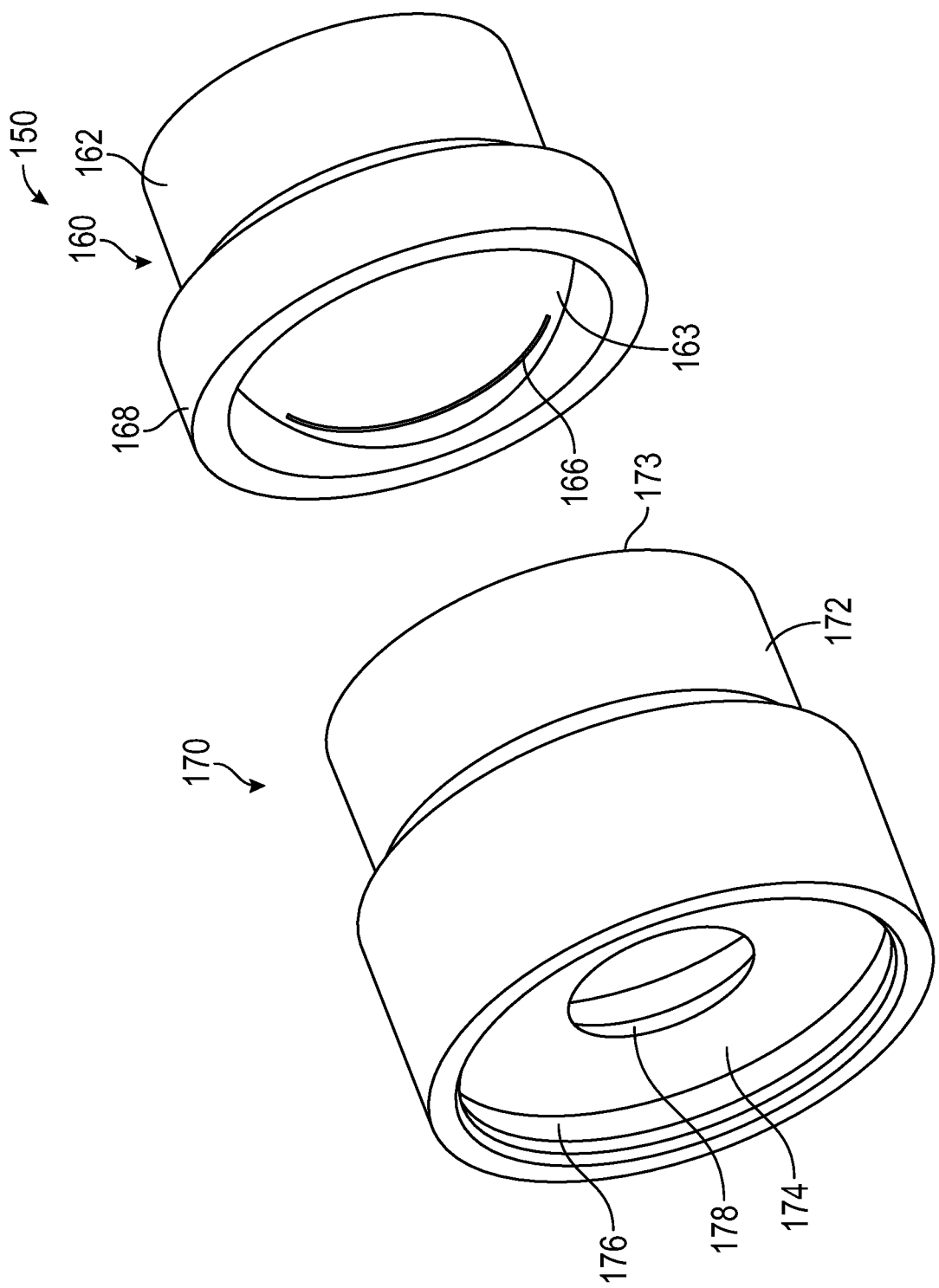
FIG. 6 is an exploded perspective view of a second connector portion of the fluid connector of FIG. 2, in accordance with aspects of the present disclosure.

FIG. 6 is an exploded perspective view of a second connector portion 150 of the fluid connector 100 of FIG. 2, in accordance with aspects of the present disclosure. With reference to FIGS. 2-4B and 6, the second connector portion 150 permits fluid flow to and from a fluid source or any other portion of the IV set. In the depicted example, the second connector portion 150 includes a connector housing 170 that allows the second connector portion 150 to be connected to a fluid source or other portion of the IV set. Tubing or a connector can be received in an opening 173 of the connector housing 170.

With reference to FIGS. 2-6, the connector housing 140 of the first connector portion 110 and the connector housing 170 of the second connector portion 150 can be coupled together to permit flow between the first connector portion 110 and the second connector portion 150. In the depicted example, the connector surface 144 of the connector housing 140 can define a valve opening 148 in fluid communication with a housing volume and the lumen 126 of the luer portion 120. Similarly, the connector surface 174 of the connector housing 170 can define a valve opening 178 in fluid connection with a housing volume and the tubing or other IV set component coupled to the opening 173 of the connector housing 170. Optionally, the connector surfaces 144, 174 can be flat or featureless to facilitate cleaning and sanitizing. As illustrated in FIG. 4B, as the first connector portion 110 and the second connector portion 150 are coupled together, fluid can flow between the valve opening 148 of the first connector portion 110 and the valve opening 178 of the second connector portion 110, allowing flow between the first connector portion 110 and the second connector portion 150.

In the depicted example, the first connector portion 110 and the second connector portion 150 can be engaged to secure or retain the first connector portion 110 and the second connector portion 150 together. As illustrated, the first connector portion 110 and the second connector portion 150 can be coupled together by inserting a portion of the first connector portion 110 into the second connector portion 150. In the depicted example, the connector housing 140 of the first connector portion 110 includes or defines a ridge 146. As illustrated, the ridge 146 extends radially outward from the connector body 142. Optionally, the ridge 146 can be located axially adjacent to the connector surface 144 that defines the valve opening 148. Similarly, the connector housing 170 of the second connector portion 150 defines a groove 176. Optionally, the groove 176 can be located axially adjacent to the connector surface 174 that defines the valve opening 178. During operation, the ridge 146 of the first connector portion 110 can engage with the groove 176 of the second connector portion 150 to couple the first connector portion 110 and the second connector portion 150.

In the depicted example, the groove 176 and the circumferential wall of the connector body 172 engages the ridge 146 of the first connector portion 110 to resist movement of the first connector portion 110 and the second connector portion 150 in a direction away from each other. Engagement of the groove 176 against the ridge 146 can, in some instances of the present disclosure, define a snap fitting or snap joint between the first connector portion 110 and the second connector portion 150.

Although the groove 176 is configured to resist separation of the first connector portion 110 and the second connector portion 150, the groove 176 and/or ridge 146 are also configured to permit separation of the first connector portion 110 and the second connector portion 150 when a threshold force exceeded between the first connector portion 110 and the second connector portion 150. In some embodiments of the present disclosure, the threshold force for separating the first connector portion 110 and the second connector portion 150 is greater than or equal to approximately five pounds (22.25 Newtons). Separation of the first connector portion 110 and the second connector portion 150 can occur when the groove 176 and/or the circumferential wall of the connector body 172 is biased or flexed in a direction away from the ridge 146. In the depicted example, the first connector portion 110 and the second connector portion 150 can separate from each other while maintaining the ability to reconnect the first connector portion 110 and the second connector portion 150 together. In some embodiments, the resistance or force to assembly and separation between the first connector portion 110 and the second connector portion 150 can be configured so that the force required for assembly of the first connector portion 110 and the second connector portion 150 is less than the force required for separation the first connector portion 110 and the second connector portion 150.

In the depicted example, the first connector portion 110 and the second connector portion 150 each include a valve member 130, 160 respectively to control flow through the connector 100. In particular, the valve members 130, 160 allow for fluid to flow between the first connector portion 110 and the second connector portion 150 when the first connector portion 110 and the second connector portion 150 are connected and prevent fluid flow when the first connector portion 110 and the second connector portion 150 are disconnected.

In the depicted example, the first connector portion 110 includes a valve member 130 disposed within the housing volume defined by the connector body 142. As illustrated, the valve body 132 can selectively restrict or obstruct flow through the connector body 142 and/or the valve opening 148. During operation, the valve body 132 can be moved, deflected, or deformed to allow flow through the connector body 142 and the valve opening 148. The valve body 132 can be formed from an elastomeric material to allow for elastic deformation of the valve body 132.

In some embodiments, the valve body 132 can define a spherical portion 133 to selectively seal, restrict, or otherwise obstruct flow through the valve opening 148. As illustrated, the spherical portion 133 can expand, seal, or engage against the connector body 142 and seal or obstruct the valve opening 148. The spherical portion 133 can be moved, deflected, or deformed to allow flow through the connector body 142 and the valve opening 148. The spherical portion 133 can include any portion of a sphere and can define a hemisphere.

As illustrated, the valve body 132 can define a slit 136 to selectively permit flow through the valve member 130 and the valve opening 148. In a first position, the edges of the slit 136 can be together to resist fluid flow through the valve body 132 and obstruct the valve opening 148. In a second position, the edges of the slit 136 can be spread apart to permit flow through the valve member 130 and through the valve opening 148.

Similarly, the second connector portion 150 includes a valve member 160 disposed within the housing volume defined by the connector body 172. As illustrated, the valve body 162 can selectively restrict or obstruct flow through the connector body 172 and/or the valve opening 178. During operation, the valve body 162 can be moved, deflected, or deformed to allow flow through the connector body 172 and the valve opening 178. The valve body 162 can be formed from an elastomeric material to allow for elastic deformation of the valve body 162.

In some embodiments, the valve body 162 can define a spherical portion 163 to selectively seal, restrict, or otherwise obstruct flow through the valve opening 178. As illustrated, the spherical portion 163 can expand, seal, or engage against the connector body 172 and seal or obstruct the valve opening 178. The spherical portion 163 can be moved, deflected, or deformed to allow flow through the connector body 172 and the valve opening 178. The spherical portion 163 can include any portion of a sphere and can define a hemisphere. In some embodiments, the valve body 162 includes a collar 168 around the spherical portion 163 to seal the valve body 162 against the connector body 172.

Optionally, the spherical portion 163 can be recessed within the collar 168 and relative to the connector body 172.

As illustrated, the valve body 162 can define a slit 166 to selectively permit flow through the valve member 160 and the valve opening 178. In a first position, the edges of the slit 166 can be together to resist fluid flow through the valve body 162 and obstruct the valve opening 178. In a second position, the edges of the slit 166 can be spread apart to permit flow through the valve member 160 and through the valve opening 178.

During operation, the valve members 130, 160 of the respective first and second connector portions 110, 150 can be moved, deflected, or deformed to control flow through the connector 100. As illustrated in FIG. 4A, when the first and second connector portions 110, 150 are spaced apart or disconnected, the valve members 130, 160 may resist fluid flow through the valve openings 148, 178. As illustrated, in FIG. 4B, when the first and second connector portions 110, 150 are engaged or coupled together, the valve members 130, 160 may contact each other and move, deflect, or deform and allow fluid flow through the valve openings 148, 178 and through the connector 100 generally. As illustrated, in some embodiments, the deformation of the valve bodies 132, 162 can allow the respective slits 136, 166 to spread apart to permit flow through the valve members 130, 160 and the valve openings 148, 178.

Figure 7:
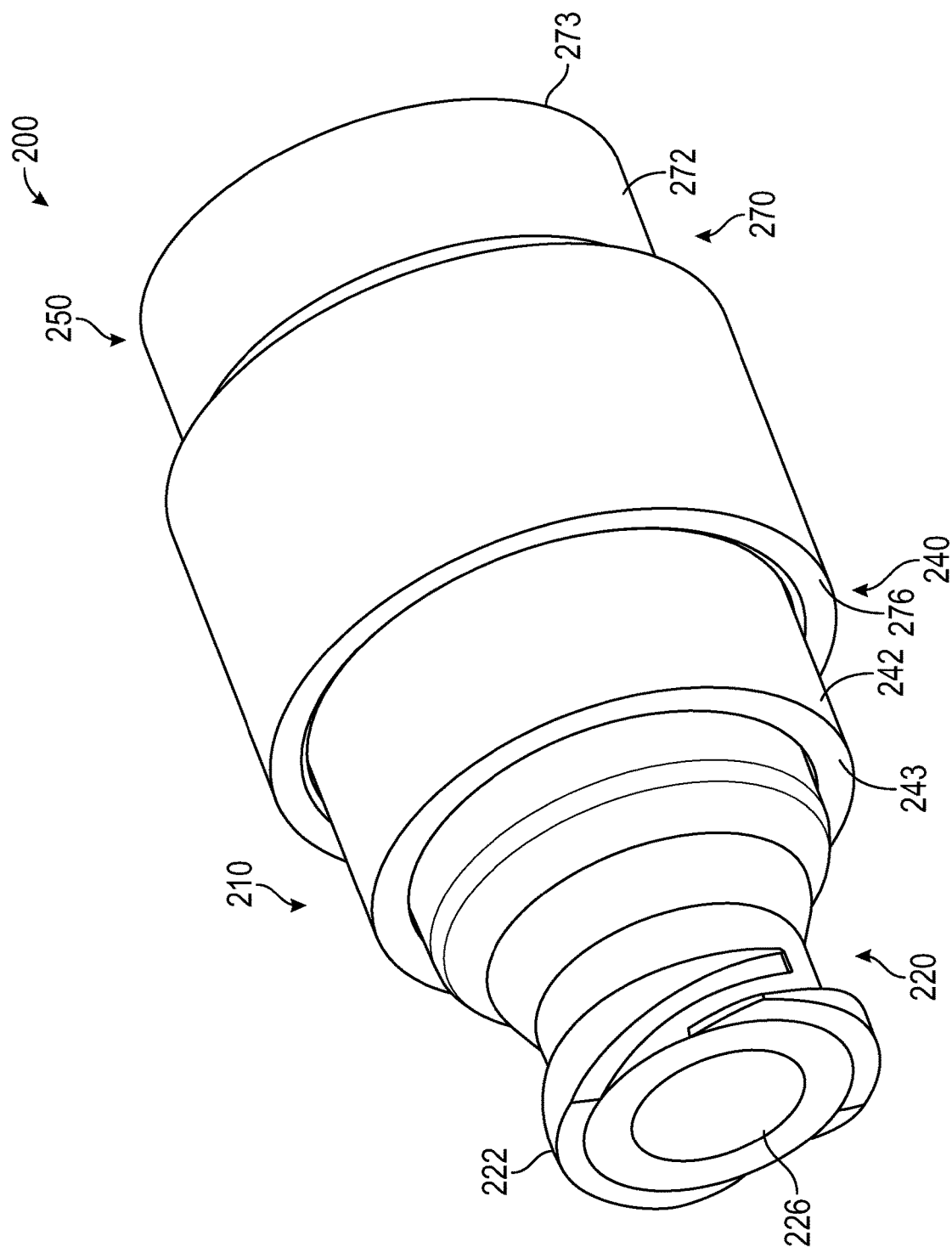
FIG. 7 illustrates a perspective view of a fluid connector, in accordance with aspects of the present disclosure.
Figure 9A:
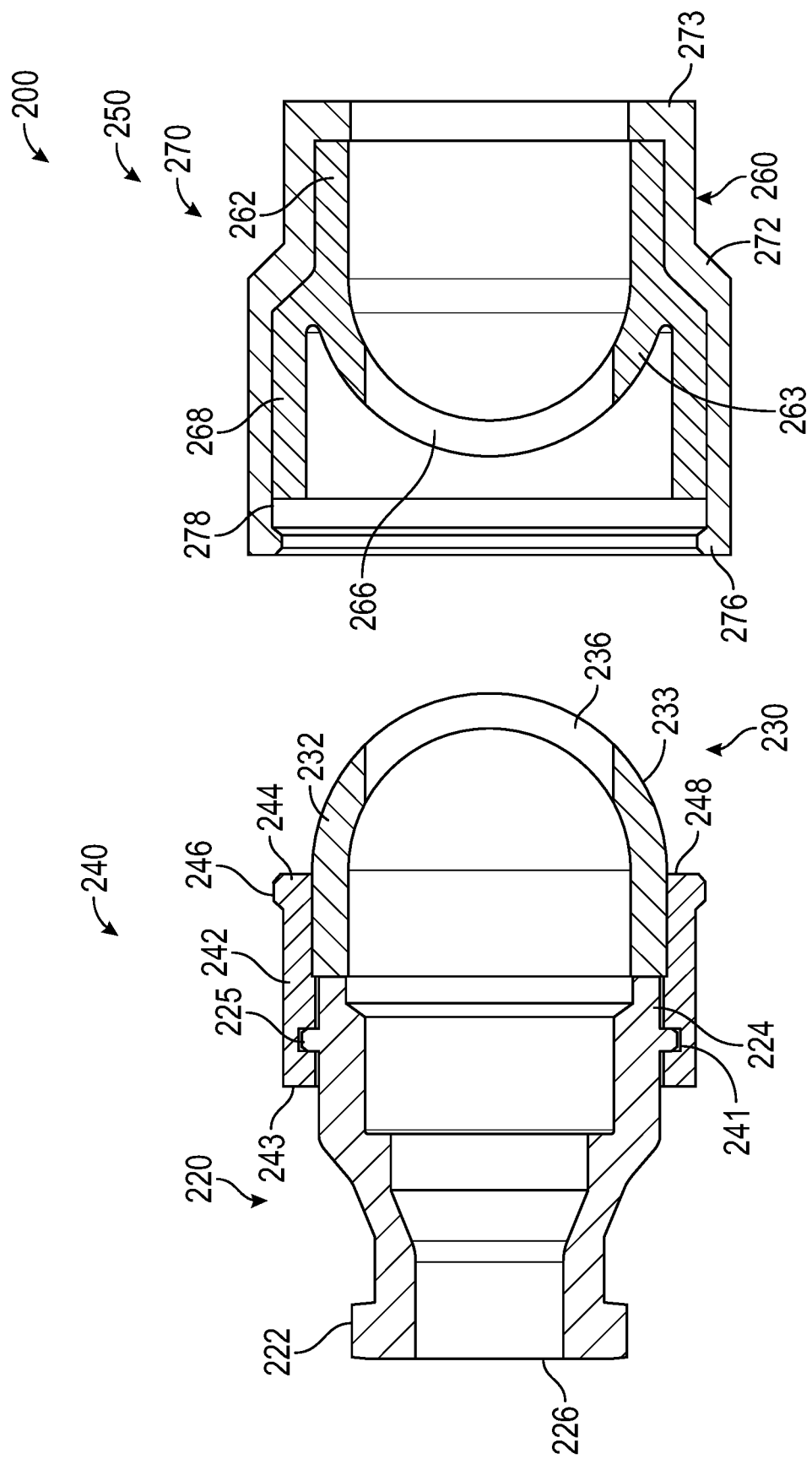
FIG. 9A illustrates a cross-sectional view of a separated fluid connector of FIG. 7, in accordance with aspects of the present disclosure.
Figure 9B:
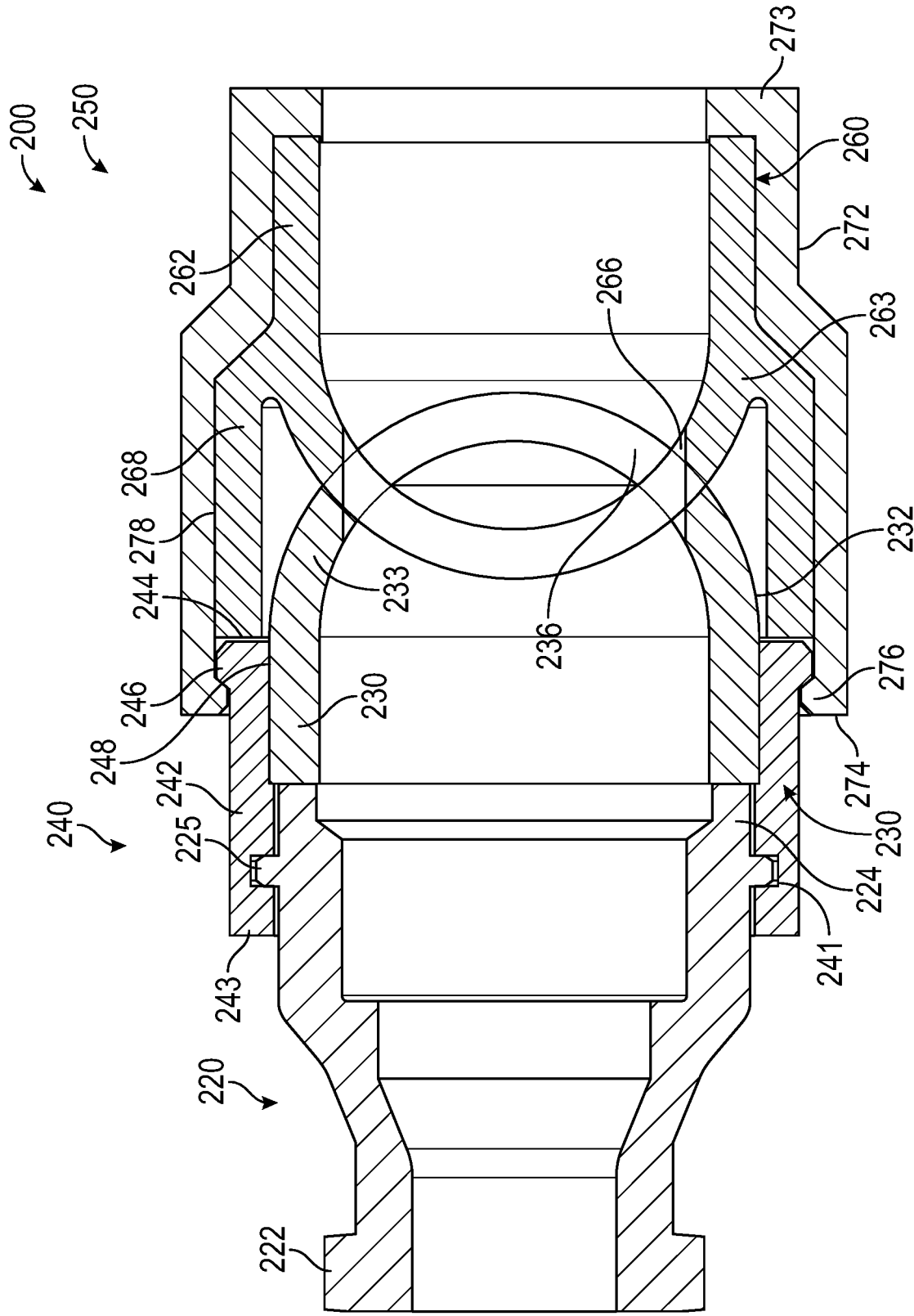
FIG. 9B illustrates a cross-sectional view of the connected fluid connector of FIG. 7, in accordance with aspects of the present disclosure.
Figure 10:
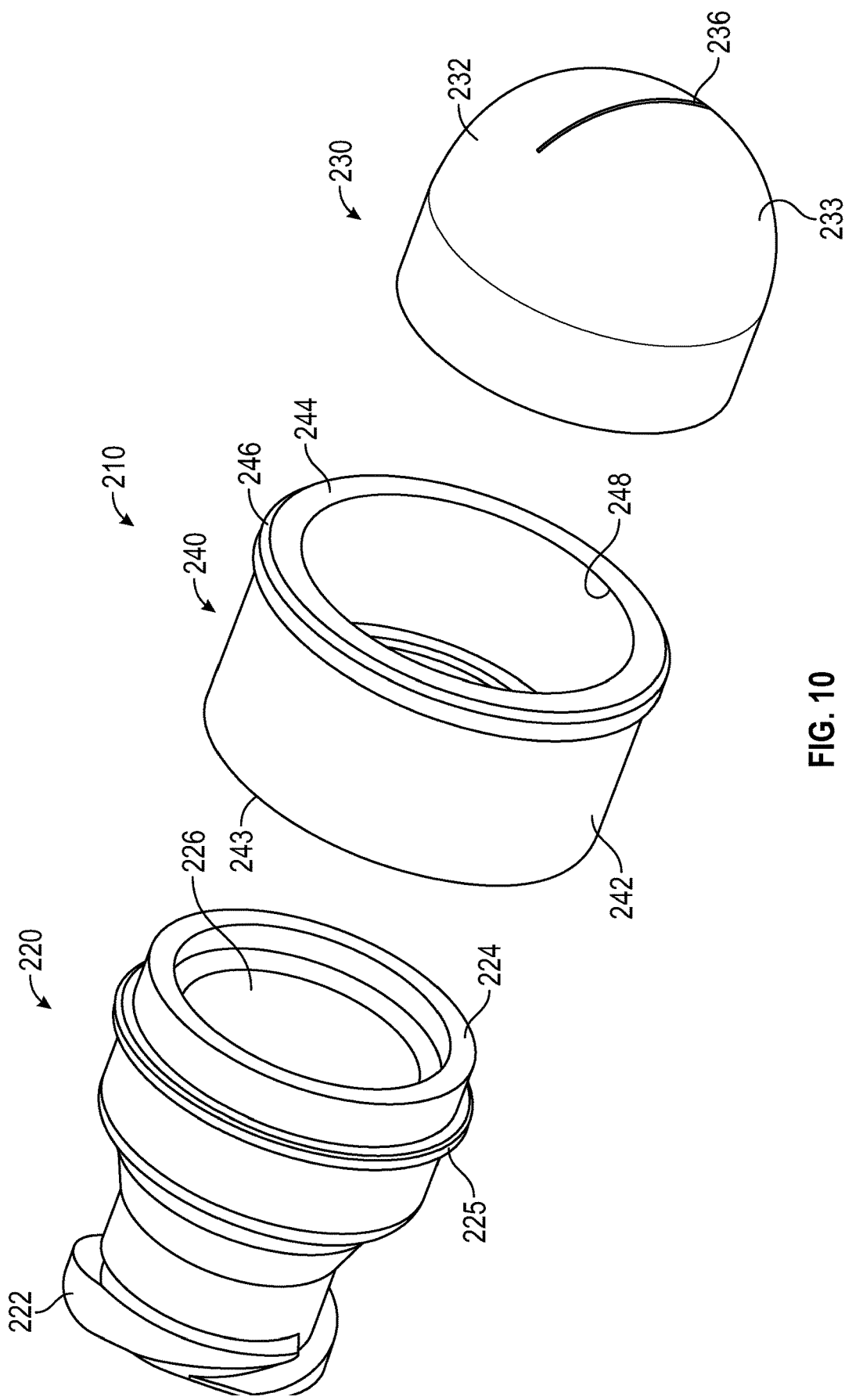
FIG. 10 is an exploded perspective view of a first connector portion of the fluid connector of FIG. 7, in accordance with aspects of the present disclosure.
Figure 11:
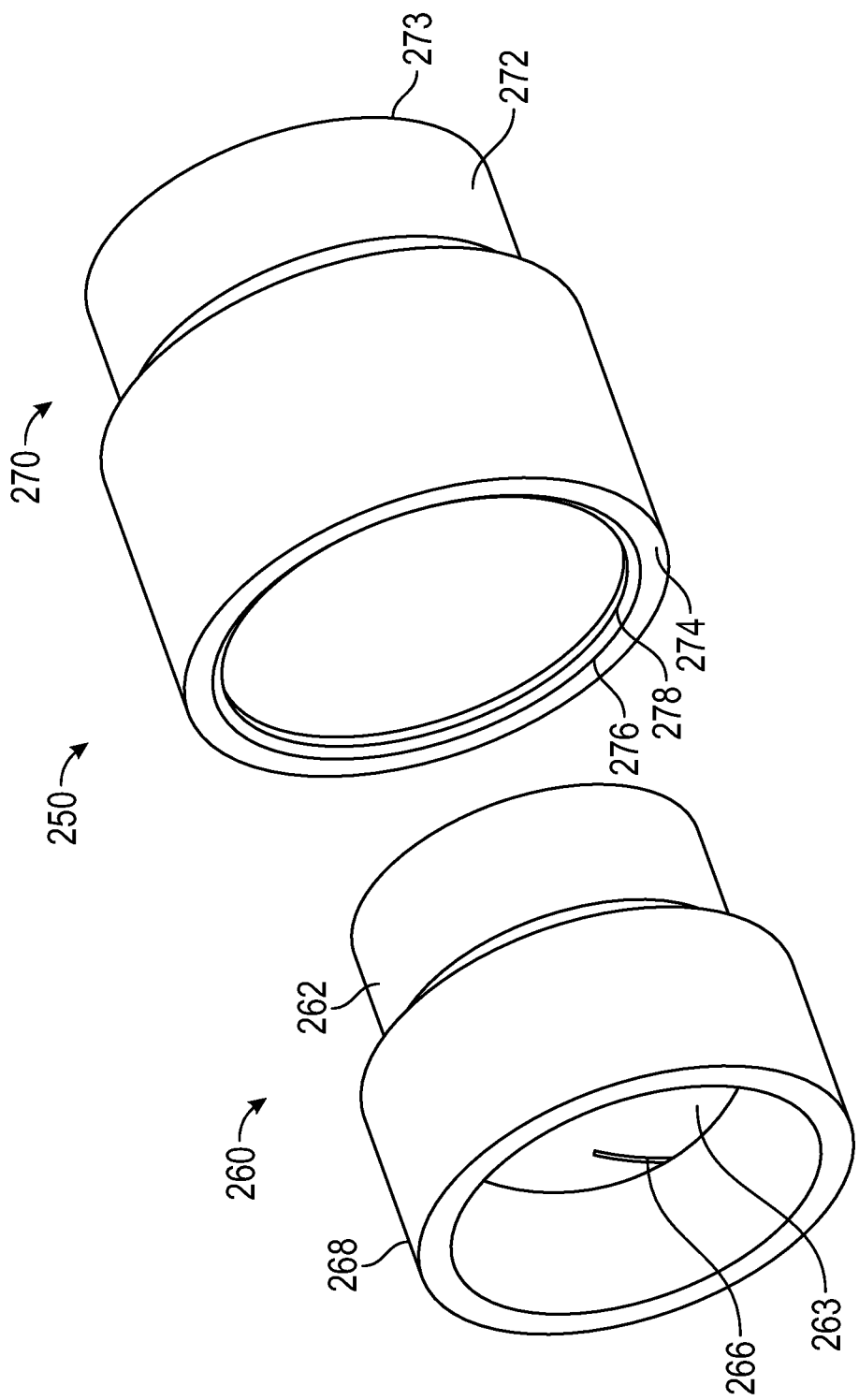
FIG. 11 is an exploded perspective view of a second connector portion of the fluid connector of FIG. 7, in accordance with aspects of the present disclosure.

FIG. 7 illustrates a perspective view of a fluid connector 200, in accordance with aspects of the present disclosure. FIG. 8 illustrates a perspective view of the connector portions 210, 250 of the fluid connector 200 of FIG. 7, in accordance with aspects of the present disclosure. FIG. 9A illustrates a cross-sectional view of a separated fluid connector 200 of FIG. 7, in accordance with aspects of the present disclosure. FIG. 9B illustrates a cross-sectional view of the connected fluid connector 200 of FIG. 7, in accordance with aspects of the present disclosure. FIG. 10 is an exploded perspective view of a first connector portion 210 of the fluid connector of FIG. 7, in accordance with aspects of the present disclosure. FIG. 11 is an exploded perspective view of a second connector portion 250 of the fluid connector of FIG. 7, in accordance with aspects of the present disclosure. With reference to FIGS. 7-11, fluid connector 200 includes certain features that are similar to fluid connector 100. Unless otherwise noted, similar features of fluid connector 200 are identified with similar reference numerals as utilized with respect to fluid connector 100. In the depicted example, the fluid connector 200 can include valve openings 248, 278 configured to expose a greater portion of the valve members 230, 260.

In the depicted example, the connector body 242 of the connector housing 240 defines a valve opening 248 at an end of the connector body 242. The valve opening 248 can be defined by the walls of the connector body 242 and disposed opposite to the luer end 243 of the connector housing 240. As illustrated, the valve opening 248 is in fluid communication with a housing volume and the lumen 226 of the luer portion 220. In some embodiments, the ridge 246 of the housing body 242 is circumferentially disposed around the valve opening 248.

As illustrated, a spherical portion 233 of the valve member 230 can extend beyond the valve opening 248 and the connector body 242 generally. Further, as illustrated, while the valve body 232 may selectively seal, restrict, or otherwise obstruct flow through the valve opening 248, the slit 236 may resist or permit flow through the valve body 232 without engaging or sealing against the valve opening 248.

Similarly, the connector body 272 of the connector housing 270 defines a valve opening 278 at an end of the connector body 272. The valve opening 278 can be defined by the walls of the connector body 272 and disposed opposite to the tubing end 273 of the connector housing 270. As illustrated, the valve opening 278 is in fluid communication with a housing volume. In some embodiments, the groove 276 of the housing body 272 is circumferentially disposed within the valve opening 278.

As illustrated, a spherical portion 263 of the valve member 260 can be recessed behind an edge of the valve opening 278 and the connector body 272 generally. Further, as illustrated, while the valve body 262 may selectively seal, restrict, or otherwise obstruct flow through the valve opening 278, the slit 266 may resist or permit flow through the valve body 262 without engaging or sealing against the valve opening 278. In some embodiments, the collar 268 of the valve member 260 can provide a sealing surface.

Figure 12:
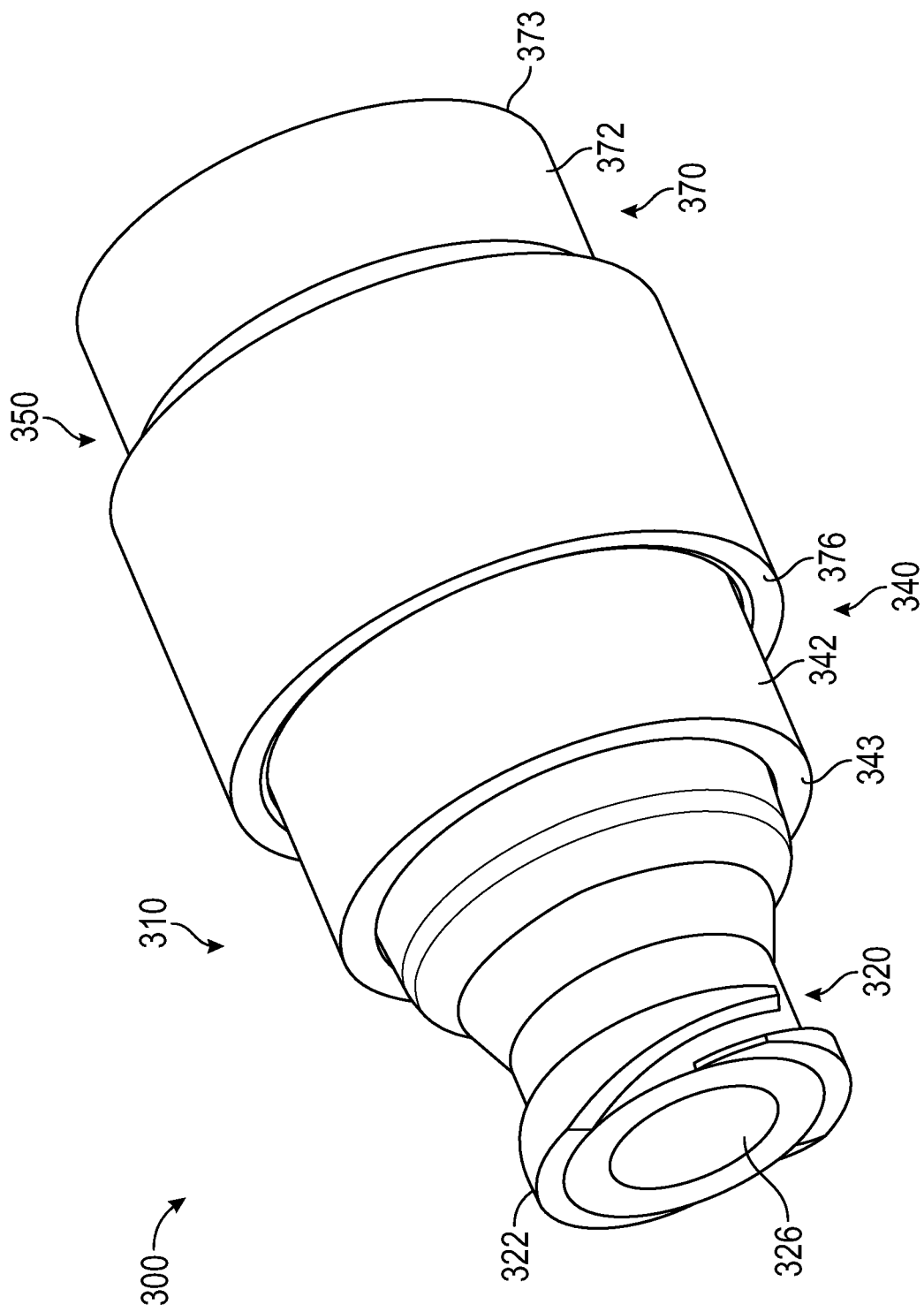
FIG. 12 illustrates a perspective view of a fluid connector, in accordance with aspects of the present disclosure.
Figure 13:
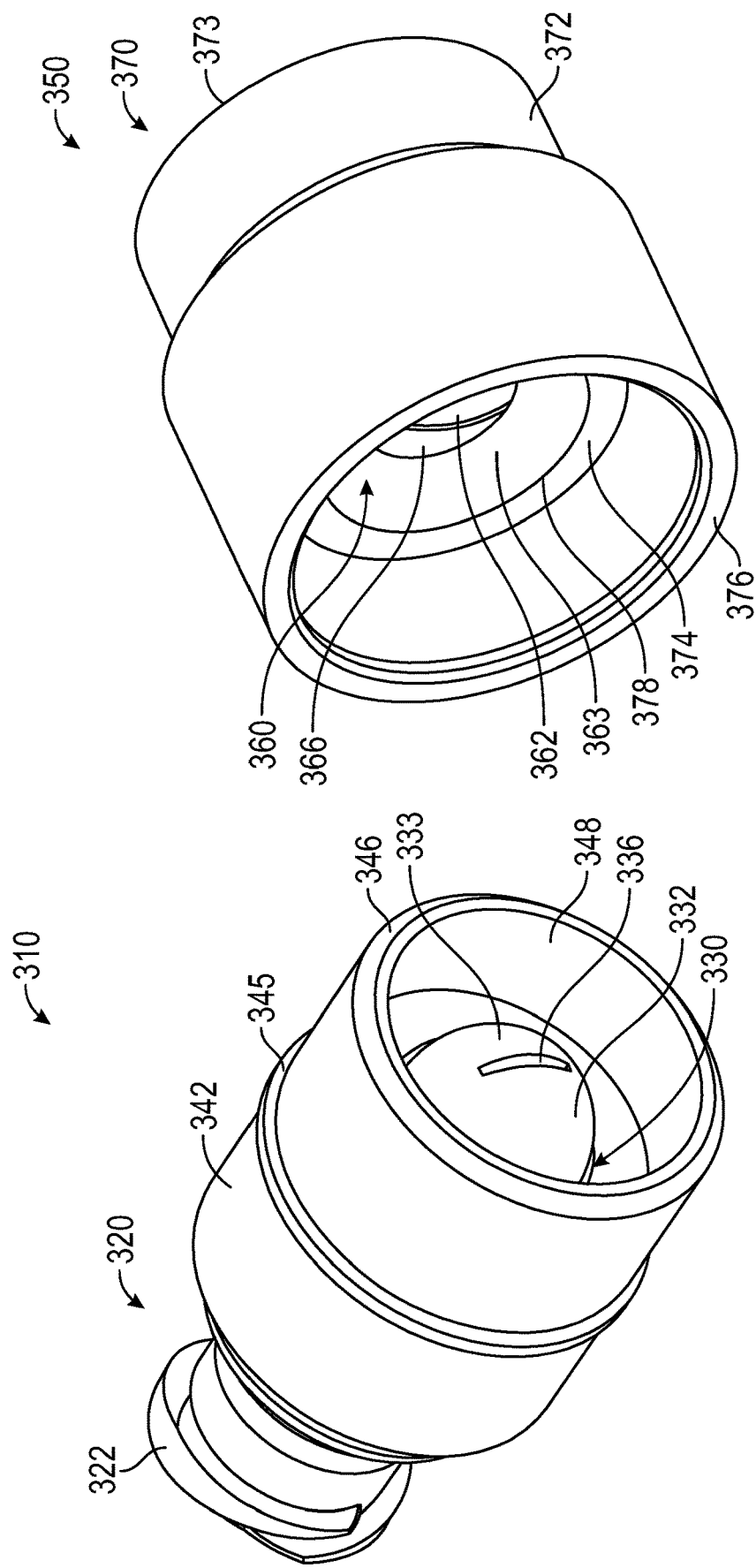
FIG. 13 illustrates a perspective view of the connector portions of the fluid connector of FIG. 12, in accordance with aspects of the present disclosure.
Figure 14A:
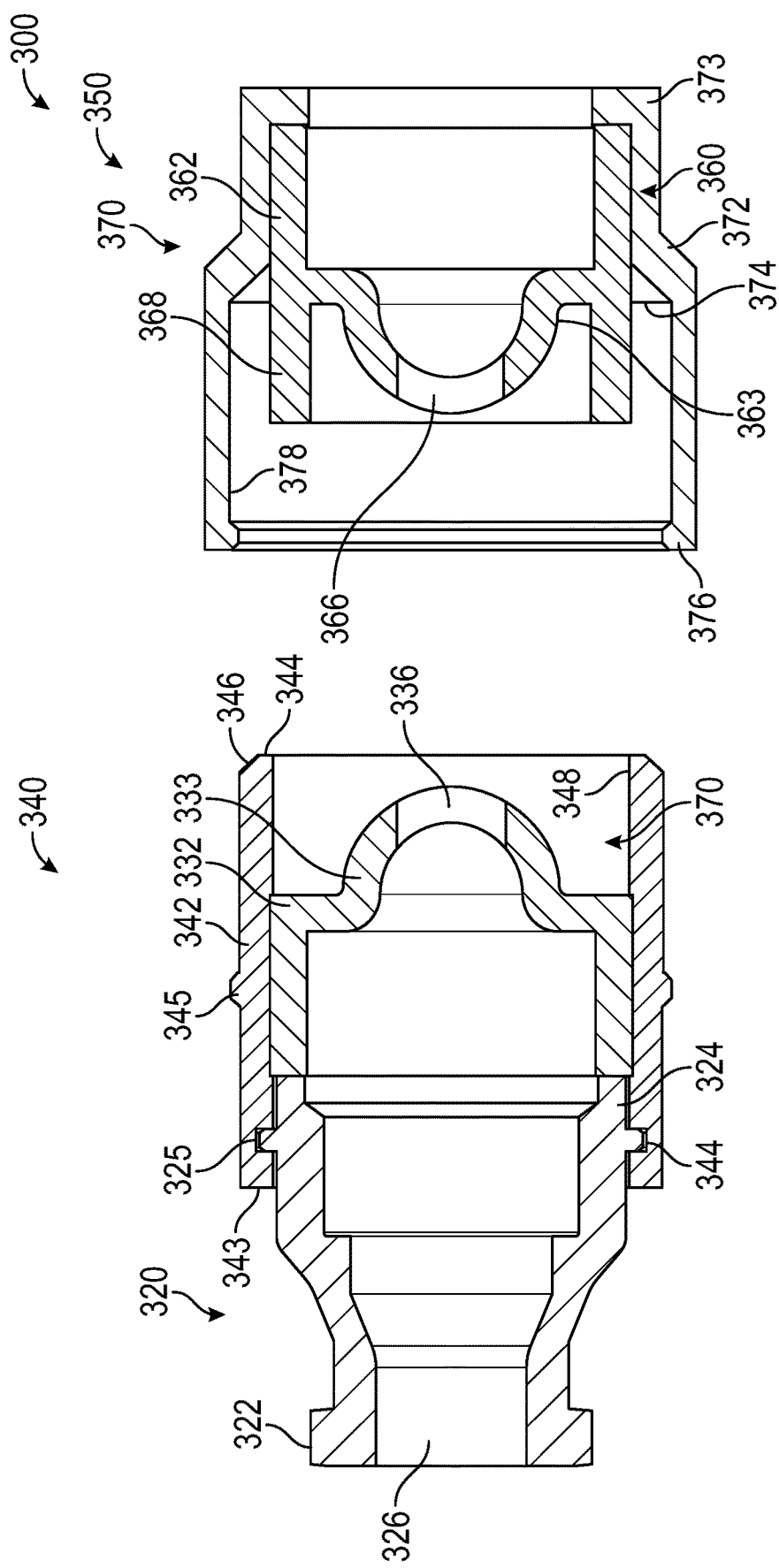
FIG. 14A illustrates a cross-sectional view of a separated fluid connector of FIG. 12, in accordance with aspects of the present disclosure.
Figure 14B:
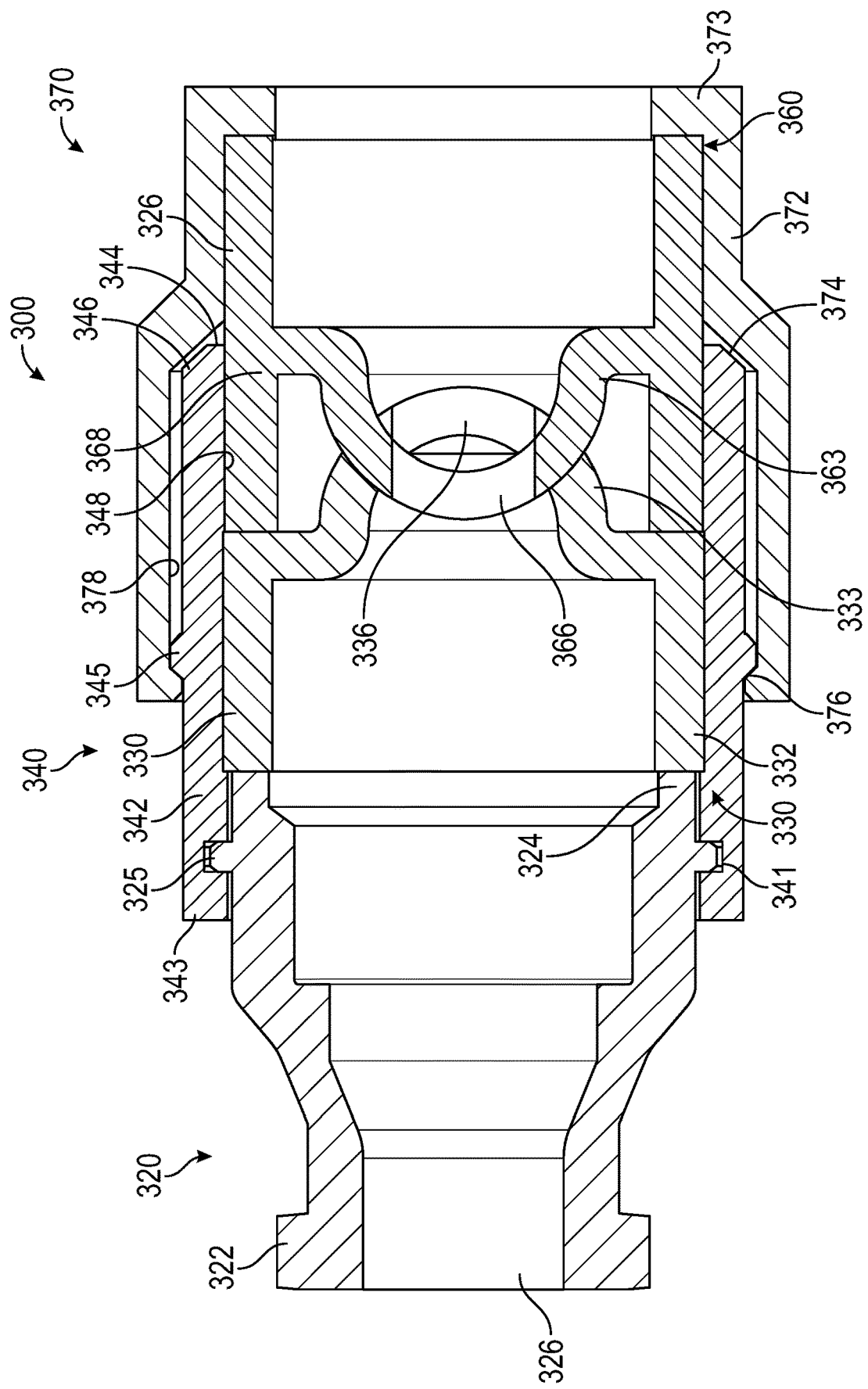
FIG. 14B illustrates a cross-sectional view of the connected fluid connector of FIG. 11, in accordance with aspects of the present disclosure.
Figure 15:
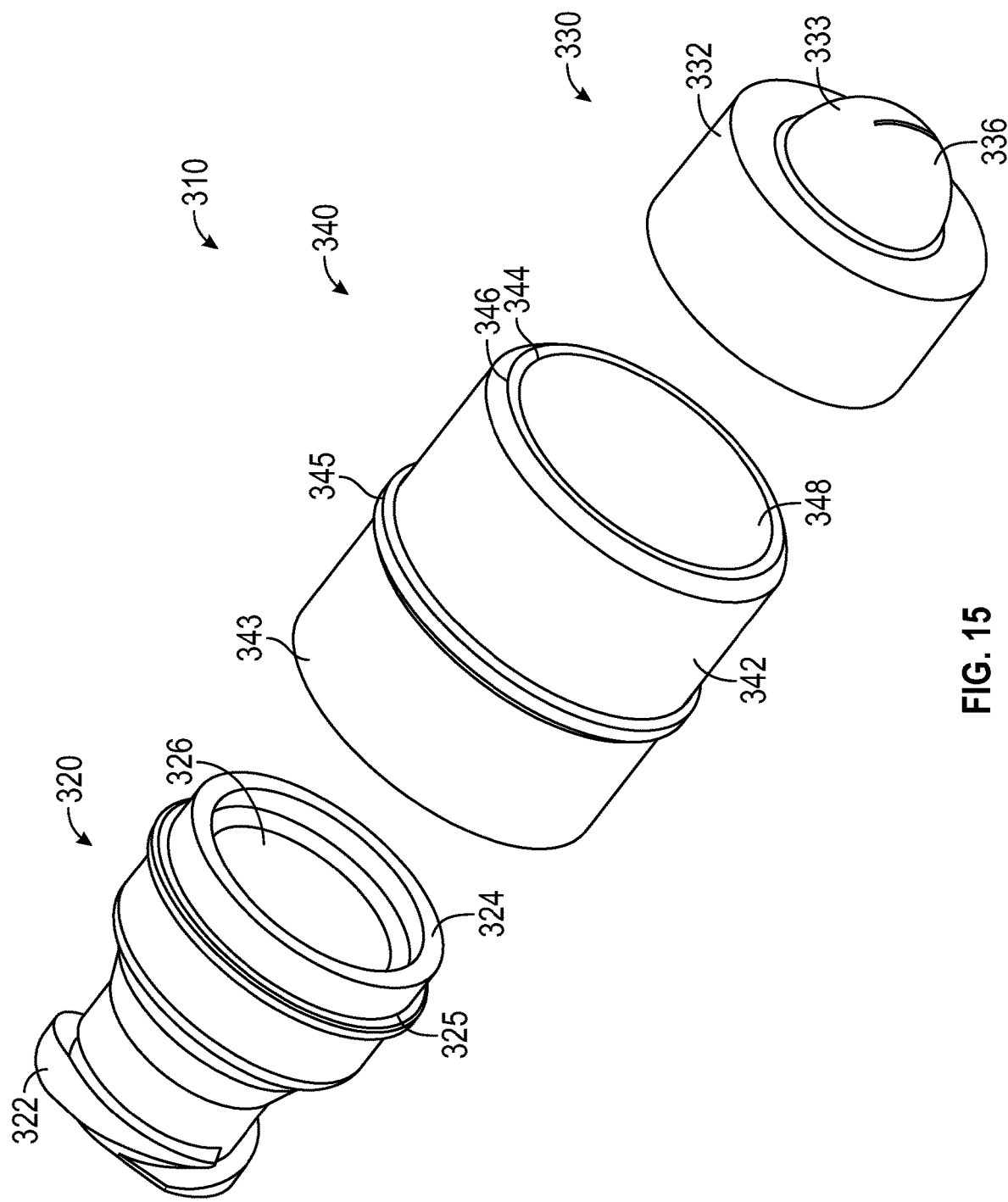
FIG. 15 is an exploded perspective view of a first connector portion of the fluid connector of FIG. 12, in accordance with aspects of the present disclosure.

FIG. 12 illustrates a perspective view of a fluid connector 300, in accordance with aspects of the present disclosure. FIG. 13 illustrates a perspective view of the connector portions 310, 350 of the fluid connector 300 of FIG. 12, in accordance with aspects of the present disclosure. FIG. 14A illustrates a cross-sectional view of a separated fluid connector 300 of FIG. 12, in accordance with aspects of the present disclosure. FIG. 14B illustrates a cross-sectional view of the connected fluid connector 300 of FIG. 11, in accordance with aspects of the present disclosure. FIG. 15 is an exploded perspective view of a first connector portion 310 of the fluid connector 300 of FIG. 12, in accordance with aspects of the present disclosure. FIG. 16 is an exploded perspective view of a second connector portion 350 of the fluid connector 300 of FIG. 12, in accordance with aspects of the present disclosure. With reference to FIGS. 12-16, fluid connector 300 includes certain features that are similar to fluid connector 100. Unless otherwise noted, similar features of fluid connector 300 are identified with similar reference numerals as utilized with respect to fluid connector 100. In the depicted example, the fluid connector 300 can include valve members 330, 360 that are recessed relative to the connector housings 340, 370 to prevent contact or contamination of the valve members 330, 360 in a separated state.

In the depicted example, the first connector portion 310 includes a valve member 330 recessed within the housing volume defined by the connector body 342. As illustrated, the valve member 330 is recessed from the valve opening 348 to prevent contact or contamination of the valve member 330 when the first connector portion 310 is separated from the second connector portion 350. In some embodiments, the walls of the connector body 342 define a collar spacing the valve member 330 away from the leading edge of the valve opening 348.

In some embodiments, the valve body 332 can define a half or hemispherical portion 333 to selectively restrict, or otherwise obstruct flow through the valve opening 348. The hemispherical portion 333 can be moved, deflected, or deformed to allow flow through the connector body 342 and the valve opening 348. Further, as illustrated, while the valve body 332 may selectively restrict, or otherwise obstruct flow through the valve opening 348, the slit 336 may resist or permit flow through the valve body 332 without engaging or sealing against the valve opening 348.

Similarly, the valve body 362 can define a half or hemispherical portion 363 to selectively restrict, or otherwise obstruct flow through the valve opening 378. The hemispherical portion 363 can be moved, deflected, or deformed to allow flow through the connector body 372 and the valve opening 378. Further, as illustrated, while the valve body 362 may selectively restrict, or otherwise obstruct flow through the valve opening 378, the slit 366 may resist or permit flow through the valve body 362 without engaging or sealing against the valve opening 378.

In the depicted example, the first connector portion 310 and the second connector portion 350 can be engaged to secure or retain the first connector portion 310 and the second connector portion 350 together. As illustrated, the first connector portion 310 and the second connector portion 350 can be coupled together by inserting a portion of the first connector portion 310 into the second connector portion 350. Compared to connector 100, a greater portion of the first connector portion 310 may be inserted into the second connector portion 350 to permit contact between the recessed valve members 330, 360 of the first and second connector portions 310, 350. In some embodiments, the connector housing 340 of the first connector portion 310 includes or defines a ridge 346 that is spaced apart from the valve opening 348 to allow the connector housing 340 to be inserted further into the connector housing 370 prior to engagement.

As illustrated, the connector housing 370 of the second connector portion 350 defines a groove 376. Optionally, the groove 376 can be located axially adjacent to the connector surface 374 that defines the valve opening 378. During operation, the ridge 346 of the first connector portion 310 can engage with the groove 376 of the second connector portion 350 to couple the first connector portion 310 and the second connector portion 350.

Figure 17:
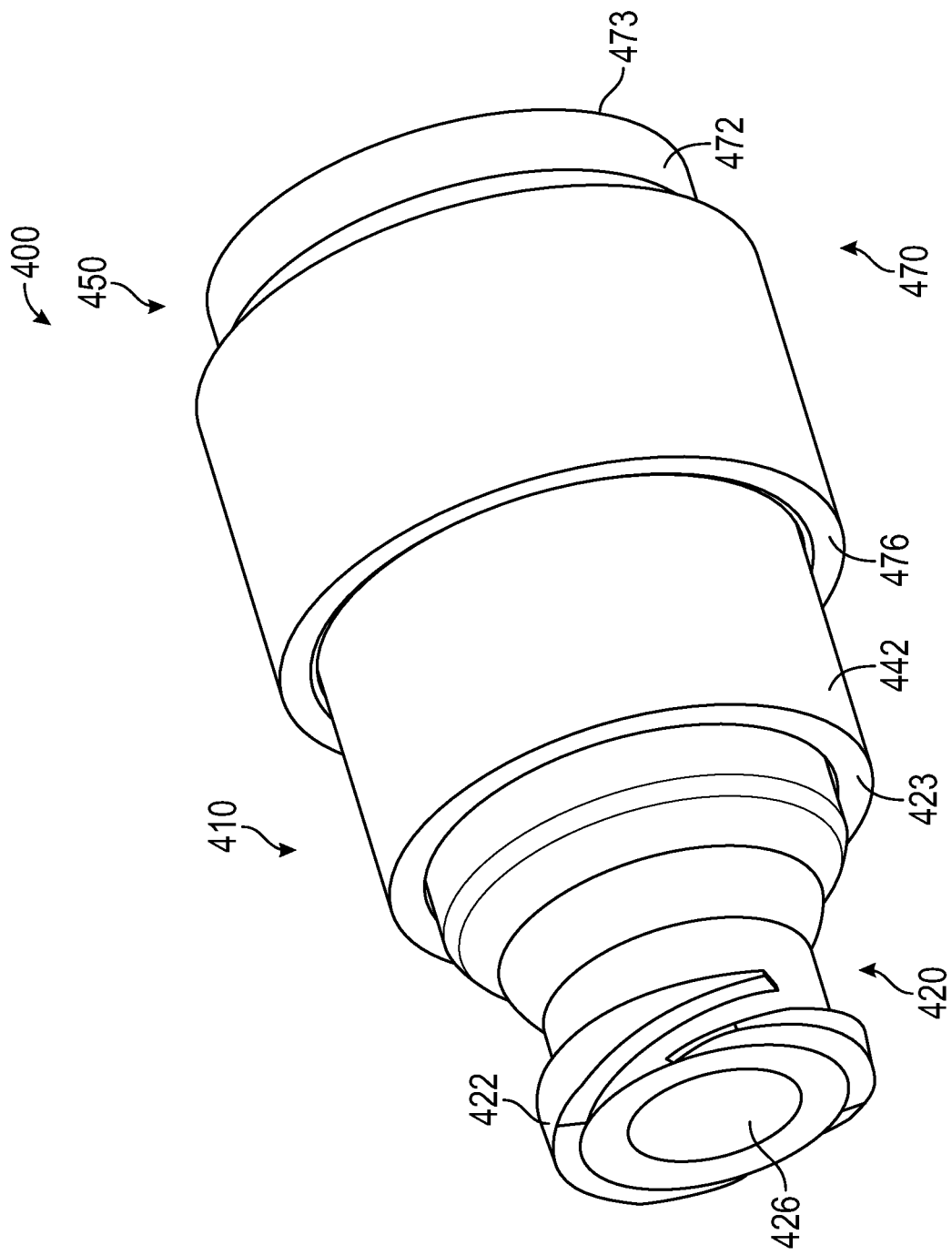
FIG. 17 illustrates a perspective view of a fluid connector, in accordance with aspects of the present disclosure.
Figure 19A:
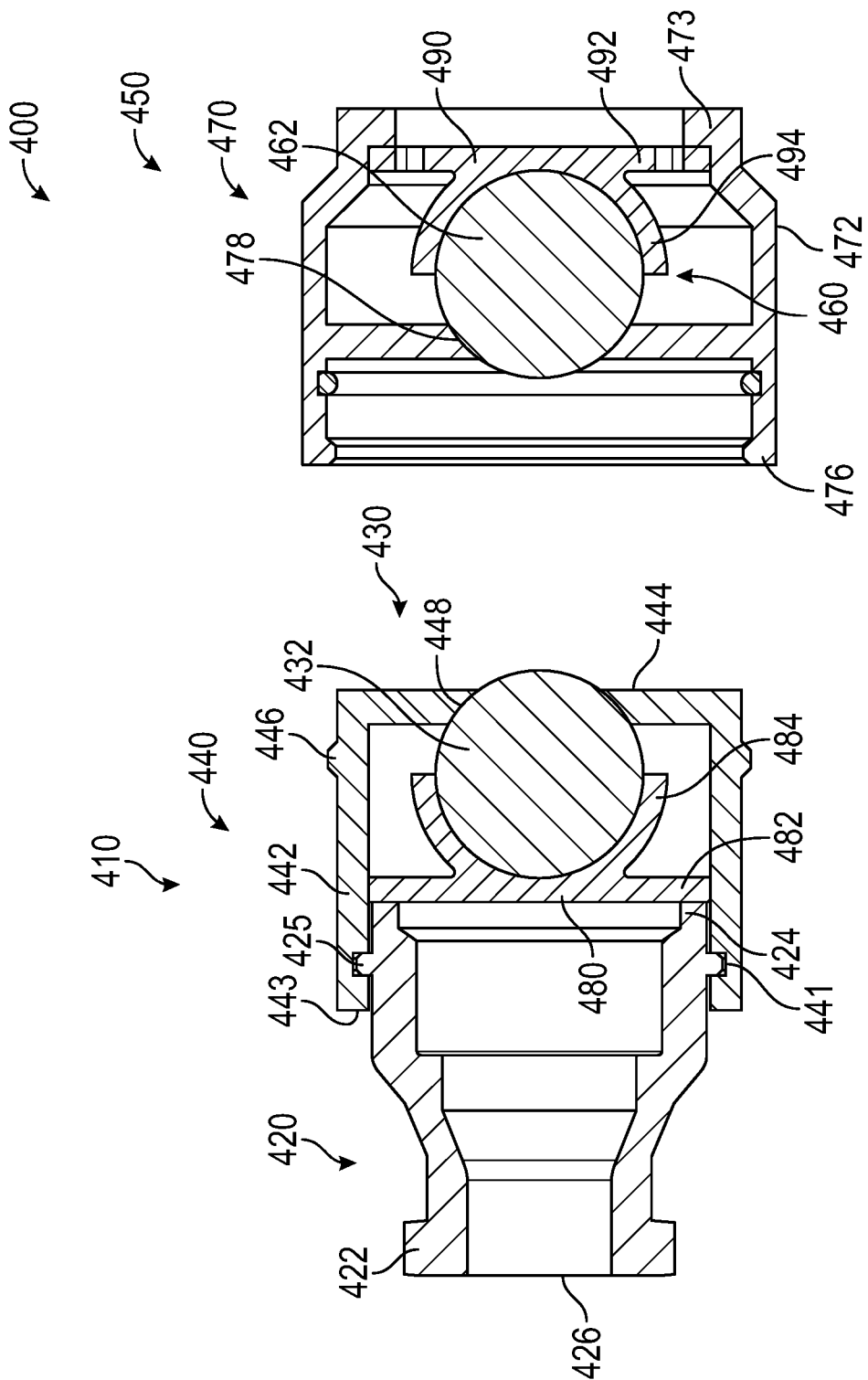
FIG. 19A illustrates a cross-sectional view of a separated fluid connector of FIG. 17, in accordance with aspects of the present disclosure.
Figure 19B:
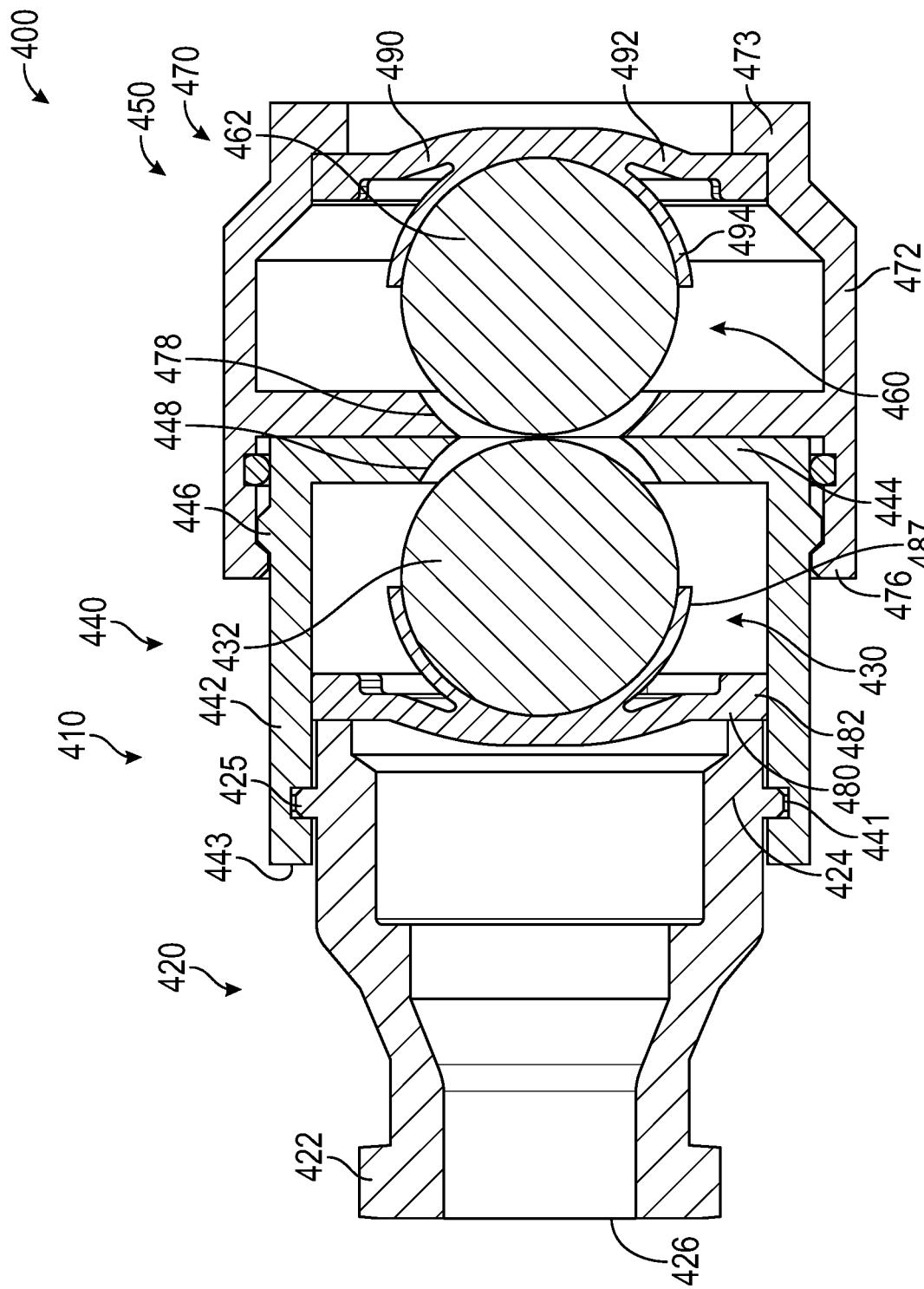
FIG. 19B illustrates a cross-sectional view of the connected fluid connector of FIG. 11, in accordance with aspects of the present disclosure.
Figure 20:
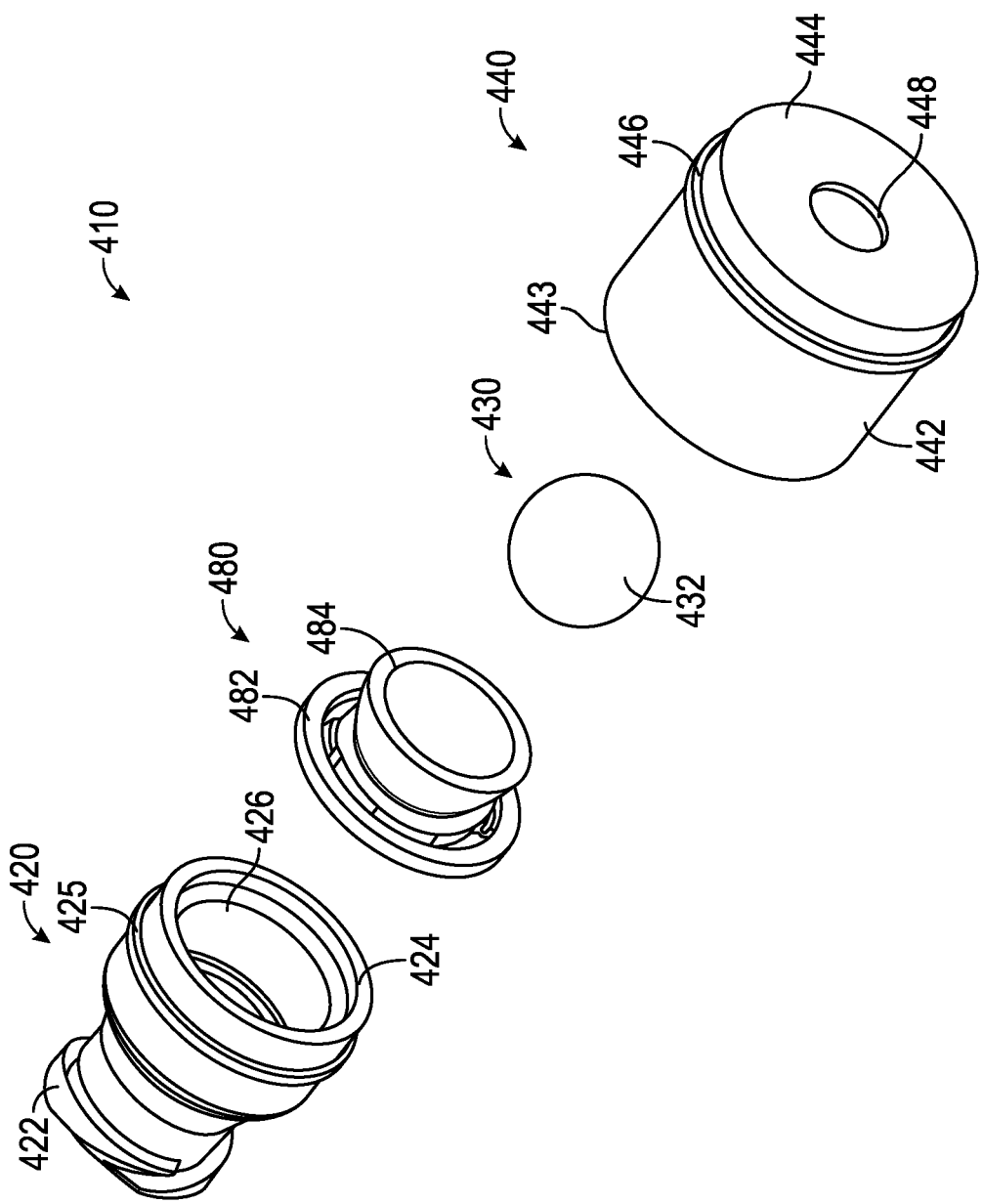
FIG. 20 is an exploded perspective view of a first connector portion of the fluid connector of FIG. 17, in accordance with aspects of the present disclosure.
Figure 21:
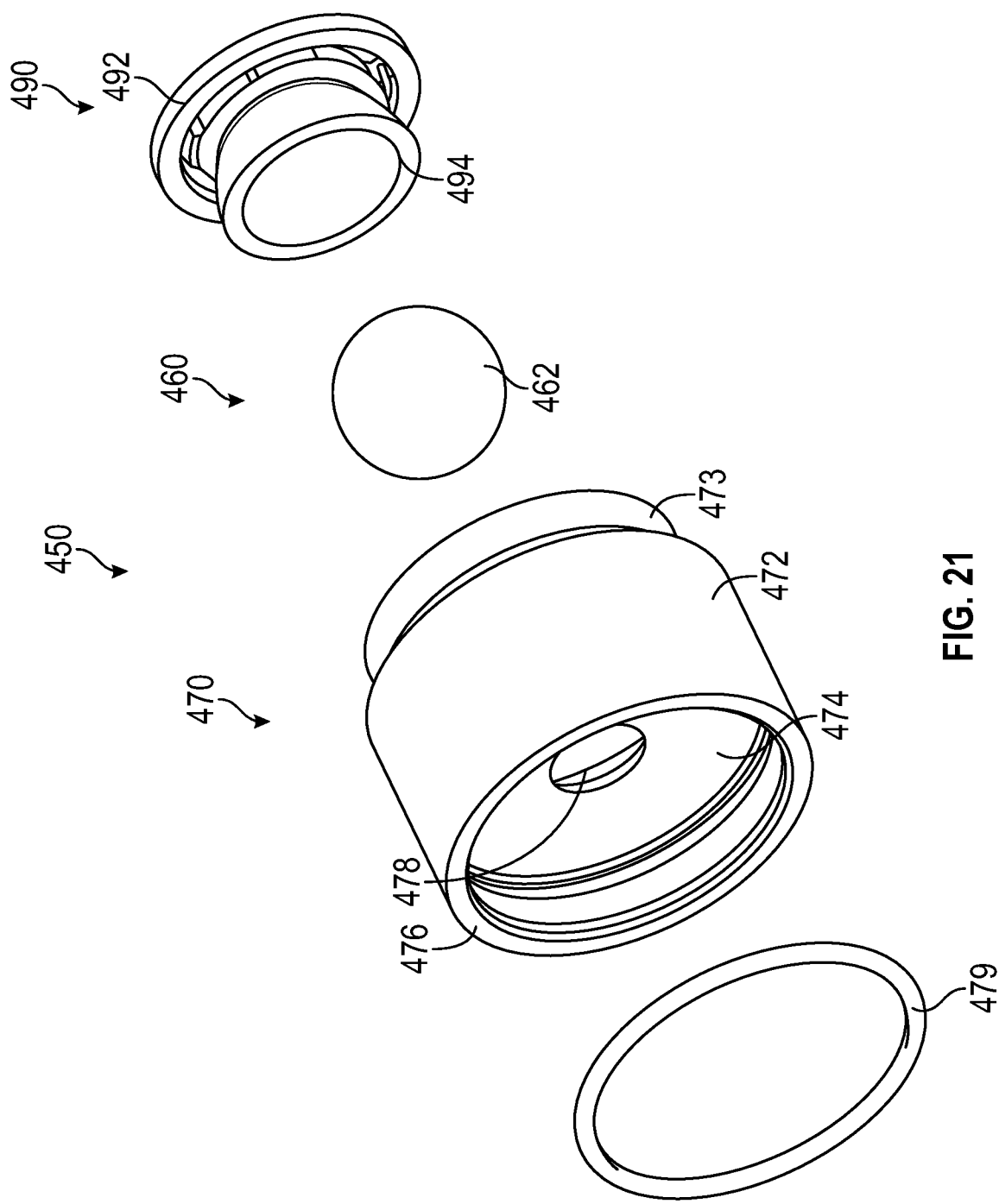
FIG. 21 is an exploded perspective view of a second connector portion of the fluid connector of FIG. 17, in accordance with aspects of the present disclosure.

FIG. 17 illustrates a perspective view of a fluid connector 400, in accordance with aspects of the present disclosure. FIG. 18 illustrates a perspective view of the connector portions 410, 450 of the fluid connector 400 of FIG. 17, in accordance with aspects of the present disclosure. FIG. 19A illustrates a cross-sectional view of a separated fluid connector 400 of FIG. 17, in accordance with aspects of the present disclosure. FIG. 19B illustrates a cross-sectional view of the connected fluid connector 400 of FIG. 17, in accordance with aspects of the present disclosure. FIG. 20 is an exploded perspective view of a first connector portion 410 of the fluid connector 400 of FIG. 17, in accordance with aspects of the present disclosure. FIG. 21 is an exploded perspective view of a second connector portion 450 of the fluid connector 400 of FIG. 17, in accordance with aspects of the present disclosure. With reference to FIGS. 17-21, fluid connector 400 includes certain features that are similar to fluid connector 100. Unless otherwise noted, similar features of fluid connector 400 are identified with similar reference numerals as utilized with respect to fluid connector 100. In the depicted example, the fluid connector 400 can utilize spherical valve members 430, 460 to control the flow through the first connector portion 410 and the second connector portion 450, respectively.

With reference to FIGS. 17-21, the first connector portion 410 and the second connector portion 450 each include a valve member 430, 460 respectively to control flow through the connector 400. In particular, the valve members 430, 460 allow for fluid to flow between the first connector portion 410 and the second connector portion 450 when the first connector portion 410 and the second connector portion 450 are connected and prevent fluid flow when the first connector portion 410 and the second connector portion 450 are disconnected. In some embodiments, the second connector portion 450 includes an O-ring 479 to allow for sealing between the first connector portion 410 and the second connector portion 450.

In the depicted example, the first connector portion 410 includes a valve member 430 disposed within the housing volume defined by the connector body 442. As illustrated, the valve body 432 can selectively restrict or obstruct flow through the connector body 442 and/or the valve opening 448. During operation, the valve body 432 can be moved or deflected to allow flow through the connector body 442 and the valve opening 448. As illustrated, the valve body 432 can define a sphere or ball to selectively seal, restrict, or otherwise obstruct flow through the valve opening 448. In a first position, the valve body 432 can engage with and obstruct the valve opening 448. In a second position, the valve body 432 can be spaced apart from the valve opening and allow flow through the valve opening 448. The valve body 432 can be formed from rigid material.

As illustrated, the valve body 432 can be biased toward the valve opening 448 to control flow through the valve opening 448. In the depicted example, a valve housing 480 can bias the valve body 432 toward the valve opening 448. As illustrated, the valve housing 480 can receive the valve body 432 in a cup 484. The valve housing body 482 and the cup 484 can bias the valve body 432 toward the valve opening 448. During operation, the valve housing 480 can be deformed or energized as the valve body 432 is displaced away from the valve opening 448. In some embodiments, the valve housing body 482 can be disposed within the housing volume of the connector housing 440. Optionally, the valve housing body 482 can include flow channels to allow fluid flow past the valve housing 480.

Similarly, the second connector portion 450 includes a valve member 460 disposed within the housing volume defined by the connector body 472. As illustrated, the valve body 462 can selectively restrict or obstruct flow through the connector body 472 and/or the valve opening 478. During operation, the valve body 462 can be moved or deflected to allow flow through the connector body 472 and the valve opening 478. As illustrated, the valve body 462 can define a sphere or ball to selectively seal, restrict, or otherwise obstruct flow through the valve opening 478. In a first position, the valve body 462 can engage with and obstruct the valve opening 478. In a second position, the valve body 462 can be spaced apart from the valve opening and allow flow through the valve opening 478. The valve body 472 can be formed from rigid material.

As illustrated, the valve body 462 can be biased toward the valve opening 478 to control flow through the valve opening 478. In the depicted example, a valve housing 490 can bias the valve body 462 toward the valve opening 478. As illustrated, the valve housing 490 can receive the valve body 462 in a cup 494. The valve housing body 492 and the cup 494 can bias the valve body 462 toward the valve opening 478. During operation, the valve housing 490 can be deformed or energized as the valve body 462 is displaced away from the valve opening 478. In some embodiments, the valve housing body 492 can be disposed within the housing volume of the connector housing 470. Optionally, the valve housing body 492 can include flow channels to allow fluid flow past the valve housing 490.

During operation, the valve members 430, 460 of the respective first and second connector portions 410, 450 can be moved or deflected to control flow through the connector 400. As illustrated in FIG. 19A, when the first and second connector portions 410, 450 are spaced apart or disconnected, the valve housings 480, 490 bias the valve members 430, 460 toward the valve openings 448, 478 to resist fluid flow through the valve openings 448, 478. As illustrated, in FIG. 19B, when the first and second connector portions 410, 450 are engaged or coupled together, the valve members 430, 460 may contact each other and move or deflect and allow fluid flow through the valve openings 448, 478 and through the connector 400 generally. As illustrated, in some embodiments, the valve housings 480, 490 can deform to allow the valve members 430, 460 to deflect or displace, allowing fluid flow through the valve openings 448, 478.

Figure 22:
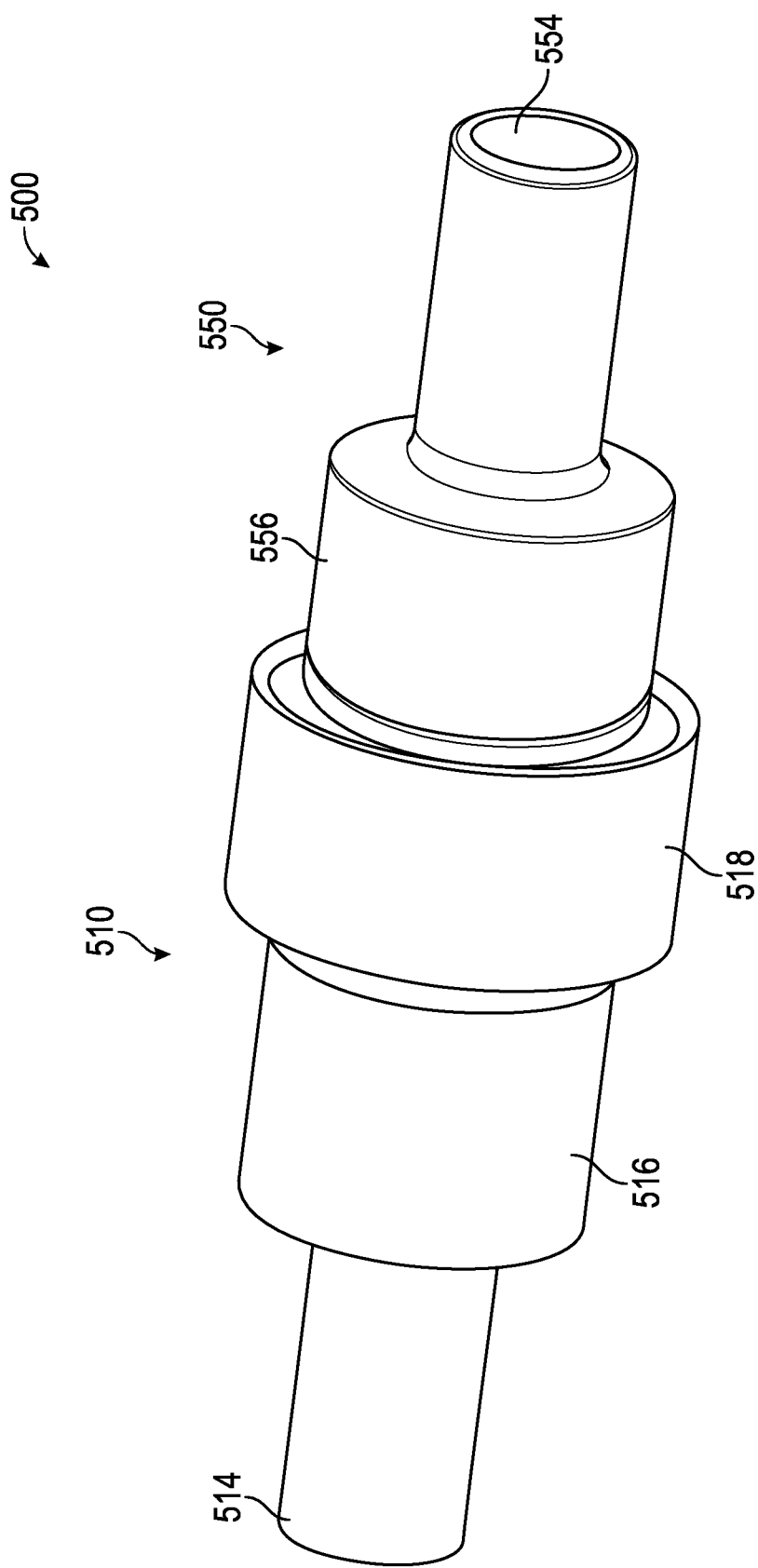
FIG. 22 illustrates a perspective view of a fluid connector, in accordance with aspects of the present disclosure.

FIG. 22 illustrates a perspective view of a fluid connector 500, in accordance with aspects of the present disclosure. FIG. 23 illustrates a cross-sectional view of the separated fluid connector 500 of FIG. 22, in accordance with aspects of the present disclosure. FIG. 24 illustrates a cross-sectional view of the connected fluid connector 500 of FIG. 24, in accordance with aspects of the present disclosure. With reference to FIGS. 22-24, the fluid connector 500 can provide a "fusible link" and utilize a flange 540 and spherical valve members 530, 570 to control the flow through the first connector portion 510 and the second connector portion 550, respectively.

In the depicted example, the fluid connector 500 provides a flow path or fluid pathway from a first end 514 to a second end 554 of the fluid connector 500. As illustrated, the fluid connector 500 includes a first connector portion 510 and a second connector portion 550 that are coupled together to form a fluid pathway.

In the depicted example, the first connector portion 510 permits fluid flow to and from the patient or any other portion of the IV set. In the depicted example, the first connector portion 510 includes a luer portion 520 to allow the first connector portion 510 to be connected to a luer connector or any other suitable connector. As illustrated, a mating connector can be attached to a first end 514. Fluid can pass to and from the fluid connector 500 through the mating connector via a lumen defined in the luer portion 520. In the depicted example, the luer portion 520 can be coupled to the connector housing 516 of the first connector portion 510.

As illustrated, the second connector portion 550 permits fluid flow to and from a fluid source or any other portion of the IV set. In the depicted example, the second connector portion 550 includes a tubing portion 560 that allows the second connector portion 550 to be connected to a fluid source or other portion of the IV set. Tubing or a connector can be received or attached to the second end 554 of the tubing portion 560.

Figure 23A:
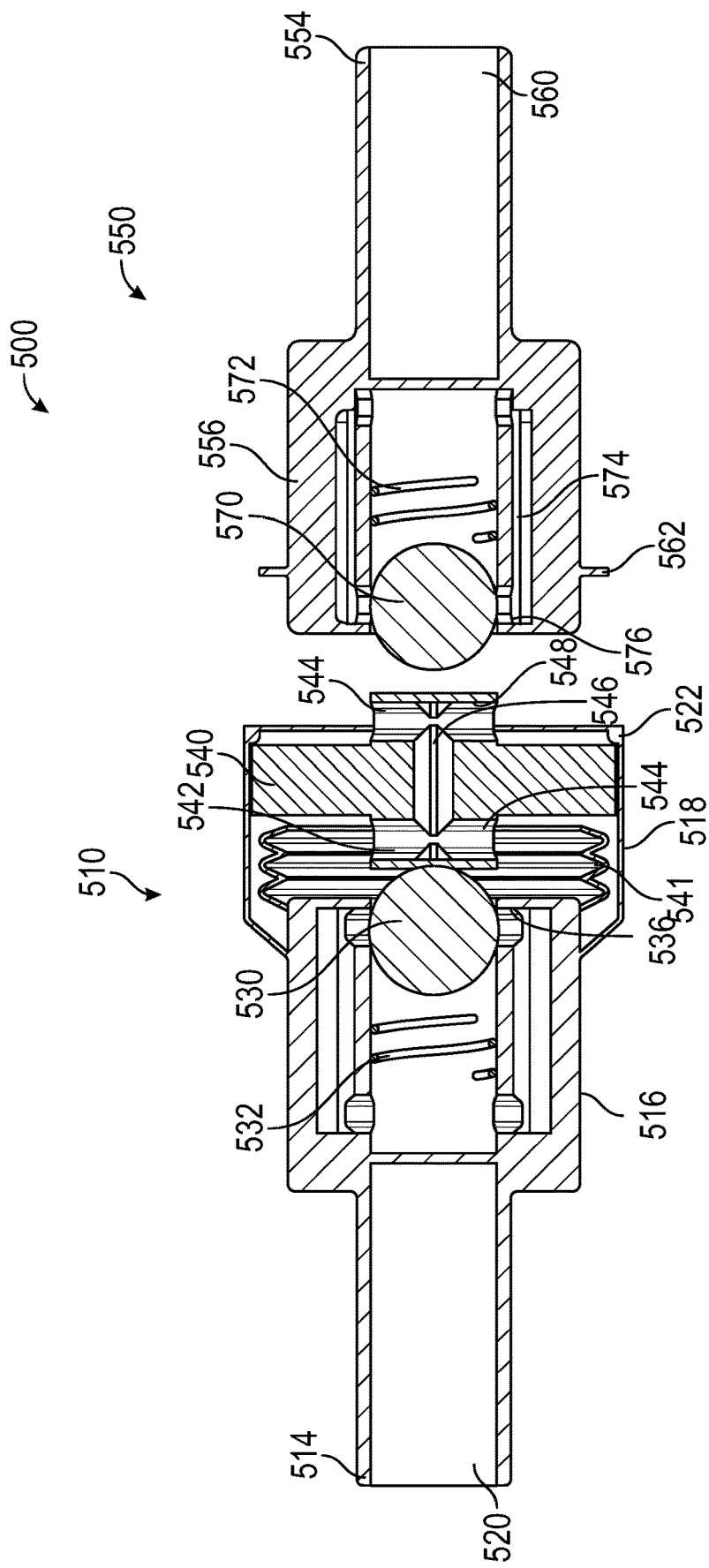
FIG. 23A illustrates a cross-sectional view of the separated fluid connector of FIG. 22, in accordance with aspects of the present disclosure.
Figure 23B:
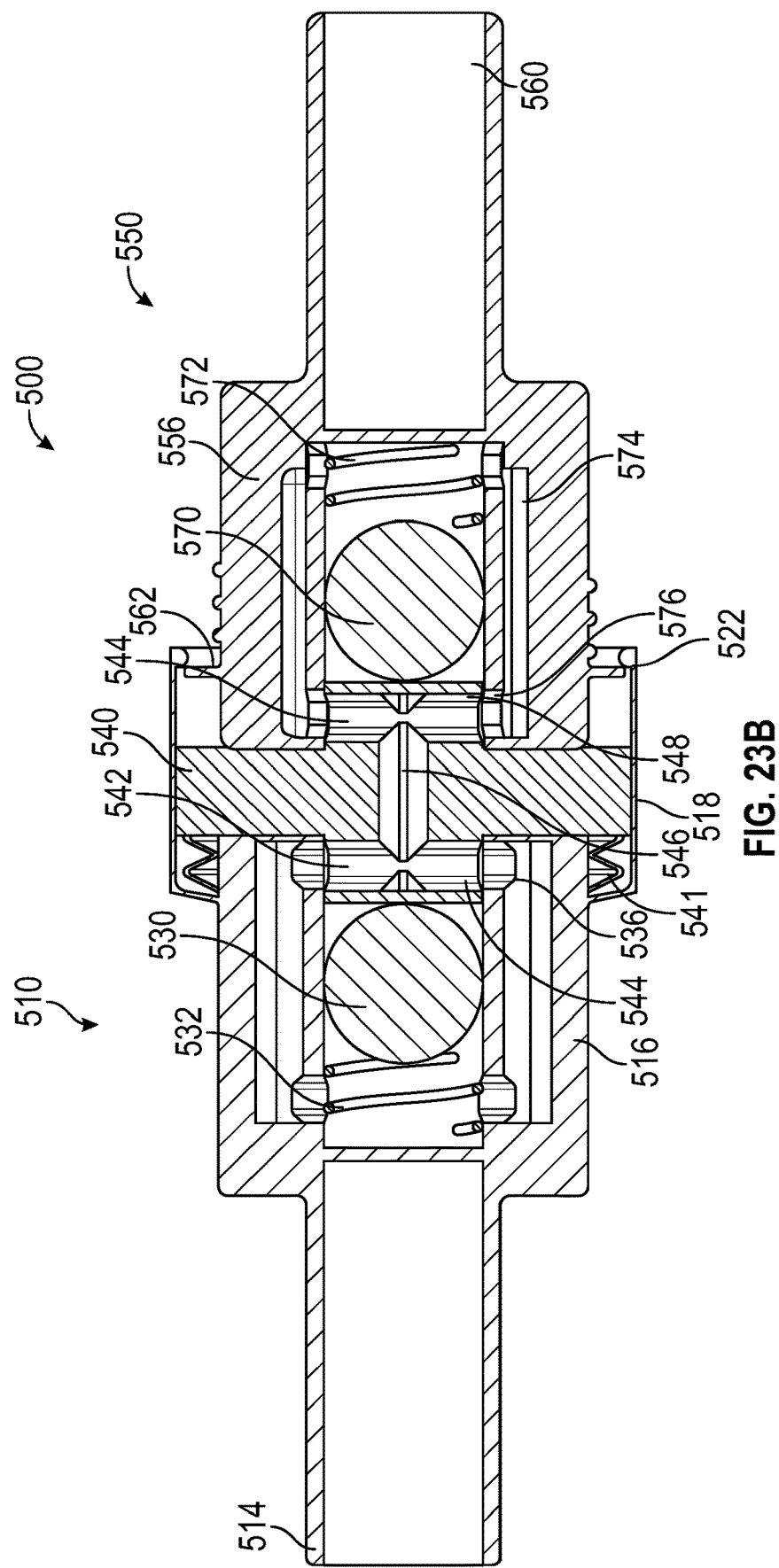
FIG. 23B illustrates a cross-sectional view of the connected fluid connector of FIG. 22, in accordance with aspects of the present disclosure.

As illustrated, the connector housing 516 of the first connector portion 510 and the connector housing 556 of the second connector housing 550 can be coupled together to permit flow between the first connector portion 510 and the second connector portion 550. In the depicted example, the connector housing 516 can define channels 534, 536 in fluid communication with the lumen of the luer portion 520. Similarly, the connector housing 556 can define channels 574, 576 in fluid communication with the lumen of the tubing portion 560. As illustrated in FIG. 23B, as the first connector portion 510 and the second connector portion 550 are coupled together, fluid can flow between the channels 536 of the first connector portion 510 and the channels 576 of the second connector portion 550, allowing flow between the first connector portion 510 and the second connector portion 550.

In the depicted example, the first connector portion 510 and the second connector portion 550 can be engaged to secure or retain the first connector portion 510 and the second connector portion 550 together. As illustrated, the first connector portion 510 and the second connector portion 550 can be coupled together by inserting a portion of the second connector portion 550 into the second connector portion 510. In the depicted example, the connector housing 556 of the second connector portion 550 includes or defines a ridge 562. As illustrated, the ridge 562 extends radially outward from the connector housing 556. Similarly, the connector housing 516 of the first connector portion 510 defines a lip 522. During operation, the ridge 562 of the second connector portion 550 can engage with the lip 522 of the first connector portion 510 to couple the first connector portion 510 and the second connector portion 550.

In the depicted example, the lip 522 and the circumferential wall of the connector housing 516 engages the ridge 562 of the second connector portion 550 to resist movement of the first connector portion 510 and the second connector portion 550 in a direction away from each other. Engagement of the lip 522 against the ridge 562 can, in some instances of the present disclosure, define a snap fitting or snap joint between the first connector portion 510 and the second connector portion 550.

Although the lip 522 is configured to resist separation of the first connector portion 510 and the second connector portion 550, the lip 522 and/or ridge 562 are also configured to permit separation of the first connector portion 510 and the second connector portion 550 when a threshold force exceeded between the first connector portion 510 and the second connector portion 550. In some embodiments of the present disclosure, the threshold force for separating the first connector portion 510 and the second connector portion 550 is greater than or equal to approximately five pounds (22.25 Newtons). Separation of the first connector portion 510 and the second connector portion 550 can occur when the lip 522 and/or the circumferential wall of the connector housing 516 is biased or flexed in a direction away from the ridge 562. In the depicted example, the first connector portion 510 and the second connector portion 550 can separate from each other while maintaining the ability to reconnect the first connector portion 510 and the second connector portion 550 together. In some embodiments, the resistance or force to assembly and separation between the first connector portion 510 and the second connector portion 550 can be configured so that the force required for assembly of the first connector portion 510 and the second connector portion 550 is less than the force required for separation the first connector portion 510 and the second connector portion 550.

In the depicted example, the first connector portion 510 and the second connector portion 550 each include a valve member 530, 570 respectively to control flow through the connector 500. In particular, the valve members 530, 570 allow for fluid to flow between the first connector portion 510 and the second connector portion 550 when the first connector portion 510 and the second connector portion 550 are connected and prevent fluid flow when the first connector portion 510 and the second connector portion 550 are disconnected.

In the depicted example, the first connector portion 510 includes a valve member 530 disposed within the housing volume defined by the connector housing 516. As illustrated, the valve member 530 can selectively restrict or obstruct flow through the connector housing 516 and/or the channels 536. During operation, the valve member 530 can be moved or deflected to allow flow through the connector housing 516 and the channels 536. As illustrated, the valve member 530 can define a sphere or ball to selectively seal, restrict, or otherwise obstruct flow through the channels 536. In a first position, the valve member 530 can engage with and obstruct the channels 536. In a second position, the valve member 530 can be spaced apart from the valve opening and allow flow through the channels 536. The valve member 530 can be formed from rigid material.

As illustrated, the valve member 530 can be biased toward the channels 536 to control flow through the channels 536. In the depicted example, a biasing member 532 can urge the valve member 530 toward the channels 536. In some embodiments, the biasing member 532 can be a spring, or any other suitable biasing member. During operation, the biasing member 532 can be deformed or energized as the valve member 530 is displaced away from the channels 536. In some embodiments, the biasing member 532 can be disposed within the housing volume of the connector housing 516.

Similarly, the second connector portion 550 includes a valve member 570 disposed within the housing volume defined by the connector housing 556. As illustrated, the valve member 570 can selectively restrict or obstruct flow through the connector housing 556 and/or the channels 576. During operation, the valve member 570 can be moved or deflected to allow flow through the connector housing 556 and the channels 576. As illustrated, the valve member 570 can define a sphere or ball to selectively seal, restrict, or otherwise obstruct flow through the channels 576. In a first position, the valve member 570 can engage with and obstruct the channels 576. In a second position, the valve member 570 can be spaced apart from the valve opening and allow flow through the channels 576. The valve member 570 can be formed from rigid material.

As illustrated, the valve member 570 can be biased toward the channels 576 to control flow through the channels 576. In the depicted example, a biasing member 572 can urge the valve member 570 toward the channels 576. In some embodiments, the biasing member 572 can be a spring, or any other suitable biasing member. During operation, the biasing member 572 can be deformed or energized as the valve member 570 is displaced away from the channels 576. In some embodiments, the biasing member 572 can be disposed within the housing volume of the connector housing 556.

During operation, the valve members 530, 570 of the respective first and second connector portions 510, 550 can be moved or deflected to control flow through the connector 500. As illustrated in FIG. 23A, when the first and second connector portions 510, 550 are spaced apart or disconnected, the biasing members 532, 572 bias the valve members 530, 570 toward the channels 536, 576 to resist fluid flow through the channels 536, 576. As illustrated, in FIG. 23B, when the first and second connector portions 510, 550 are engaged or coupled together, the valve members 530, 570 may move or deflect and allow fluid flow through the channels 536, 576 and through the connector 500 generally. As illustrated, in some embodiments, the biasing members 532, 572 can compress to allow the valve members 530, 570 to deflect or displace, allowing fluid flow through the channels 536, 576.

In the depicted example, the first connector portion 510 includes a flange 540 to facilitate the transfer of fluid between the first connector portion 510 and the second connector portion 550. As illustrated, when the first connector portion 510 and the second connector portion 550 are connected, the flange 540 can displace the valve members 530, 570 and direct fluid flow between the channels 536, 576. In the depicted example, the flange 540 includes protrusions 542, 544 to engage or displace valve members 530, 570, respectively. In some embodiments, the flange 540 further defines channels 543, 546, 545 to permit fluid flow through or across the flange 540. As illustrated, the channels 543 can be formed in protrusion 542, channel 546 can be formed in the main body of the flange 540, and channels 545 can be formed in protrusion 544. In some applications, the channels 543 are configured to be in selective fluid contact with the channels 536 when the valve member 530 is displaced by protrusion 542 and channels 545 are configured to be in selective fluid contact with the channels 576 when the valve member 570 is displaced by the protrusion 544.

As illustrated in FIG. 23A, when the first and second connector portions 510, 550 are spaced apart or disconnected, a flange biasing member 541 can space the flange 540 and protrusion 542 away from the valve member 530, preventing or resisting flow across the flange 540. As illustrated, in FIG. 23B, when the first and second connector portions 510, 550 are engaged or coupled together, the protrusions 542, 544 of the flange 540 may move or deflect the valve members 530, 570 and allow fluid flow from the channels 536, 576 to pass through channels 543, 546, 545 of the flange 540, permitting flow through the connector 500 generally.

Illustration of Subject Technology as Clauses

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. A connector comprising: a first connector portion comprising: a connector housing comprising a connector body defining a housing volume, a luer opening and a valve opening, wherein the housing volume is in fluid communication with the luer opening and the valve opening; a luer portion comprising a luer end and a housing end, the luer portion defining a lumen extending between the luer end and the housing end, wherein the housing end of the luer portion extends through the luer opening of the connector body to couple the luer portion to the connector housing and the lumen is in fluid communication with the housing volume; and a deformable valve member disposed within the housing volume and comprising a spherical portion extending partially through the valve opening, wherein the spherical portion defines a slit, and the deformable valve member is configured to selectively prevent fluid flow from the housing volume through the valve opening and to deform to expand the slit and permit fluid flow from the housing volume through the valve opening.

Clause 2. The connector of Clause 1, wherein the deformable valve member comprises an elastomeric material.

Clause 3. The connector of Clause 1, wherein the spherical portion of the deformable valve member comprises a hemispherical shape.

Clause 4. The connector of Clause 1, wherein the connector body comprises a planar connector surface and the valve opening is defined through the planar connector surface.

Clause 5. The connector of Clause 1, wherein the luer opening and the valve opening are equal in diameter.

Clause 6. The connector of Clause 1, wherein the connector body comprises a collar extending axially beyond the spherical portion of the deformable valve member.

Clause 7. The connector of Clause 1, wherein the luer portion is releasably coupled to the connector housing.

Clause 8. The connector of Clause 1, wherein the connector housing and the luer portion retain the deformable valve member within the housing volume.

Clause 9. The connector of Clause 1, further comprising: a second connector portion comprising: a second connector housing comprising a second connector body defining a second housing volume, a tubing opening and a second valve opening, wherein the second housing volume is in fluid communication with the tubing opening and the second valve opening; and a second deformable valve member disposed within the second housing volume and comprising a second spherical portion extending partially through the second valve opening, wherein the second spherical portion defines a second slit, and wherein the connector portion and the second connector portion are configured to be releasably coupled, the deformable valve member and the second deformable valve member are configured to selectively prevent fluid flow through the respective housing volume and the second housing volume when the first and second connector portions are spaced apart and to deform to expand the slit and the second slit and permit fluid flow between the first and second connector portions when the first and second connector portions are coupled and the deformable valve member and the second deformable valve member are in contact.

Clause 10. The connector of Clause 9, wherein the connector housing further comprises an engagement lip extending radially from the connector body, and the second connector housing comprises an engagement groove disposed around the second connector body, and the engagement lip is configured to releasably engage the engagement groove.

Clause 11. The connector of Clause 9, wherein the first and second connector portion are configured to separate with about 5 pounds of force.

Clause 12. A connector comprising: a first connector portion comprising: a connector housing comprising a connector body defining a housing volume, a luer opening and a valve opening, wherein the housing volume is in fluid communication with the luer opening and the valve opening; a luer portion comprising a luer end and a housing end, the luer portion defining a lumen extending between the luer end and the housing end, wherein the housing end of the luer portion extends through the luer opening of the connector body to couple the luer portion to the connector housing and the lumen is in fluid communication with the housing volume; and a spherical valve member disposed within the housing volume, wherein the spherical valve member is configured to selectively obstruct the valve opening to prevent fluid flow from the housing volume through the valve opening and to displace away from the valve opening and permit fluid flow from the housing volume through the valve opening.

Clause 13. The connector of Clause 12, wherein the first connector portion comprises a valve housing coupled to the spherical valve member, and the valve housing is configured to urge the spherical valve member toward the valve opening.

Clause 14. The connector of Clause 13, wherein the connector housing and the luer portion retain the valve housing within the housing volume.

Clause 15. The connector of Clause 13, wherein the valve housing defines at least one channel and the at least one channel is configured to permit flow through the connector housing.

Clause 16. The connector of Clause 12, wherein the connector body comprises a planar connector surface and the valve opening is defined through the planar connector surface.

Clause 17. The connector of Clause 12, wherein the luer portion is releasably coupled to the connector housing.

Clause 18. The connector of Clause 12, further comprising: a second connector portion comprising: a second connector housing comprising a second connector body defining a second housing volume, a tubing opening and a second valve opening, wherein the second housing volume is in fluid communication with the tubing opening and the second valve opening; and a second spherical valve member disposed within the second housing volume; and wherein the first and second connector portion are configured to be releasably coupled, the spherical valve member and the second spherical valve member are configured to selectively prevent fluid flow through the respective housing volume and the second housing volume when the first and second connector portions are spaced apart and to displace the spherical valve member and the second spherical valve member away from the respective valve opening and the second valve opening and permit fluid flow between the first and second connector portions when the first and second connector portions are coupled and the spherical valve member and the second spherical valve member are in contact.

Clause 19. The connector of Clause 18, wherein the connector housing further comprises an engagement lip extending radially from the connector body, and the second connector housing comprises an engagement groove disposed around the second connector body, and the engagement lip is configured to releasably engage the engagement groove.

Clause 20. A connector comprising: a connector housing comprising a connector body defining a housing volume, a luer opening and a valve opening, wherein the housing volume is in fluid communication with the luer opening and the valve opening; a luer portion comprising a luer end and a housing end, the luer portion defining a lumen extending between the luer end and the housing end, wherein the housing end of the luer portion extends through the luer opening of the connector body to couple the luer portion to the connector housing and the lumen is in fluid communication with the housing volume; a spherical valve member disposed within the housing volume; and a movable flange movably coupled to the connector housing, wherein the movable flange comprises a protrusion defining a flange channel, wherein the spherical valve member is configured to selectively prevent flow through the housing volume when the protrusion of the movable flange and the spherical valve member are spaced apart and to displace the spherical valve member away from the valve opening and permit fluid flow between the valve opening and the flange channel when the spherical valve member and the protrusion of the flange are in contact.

FURTHER CONSIDERATIONS

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

In one aspect, the term "coupled" or the like may refer to being directly coupled. In another aspect, the term "coupled" or the like may refer to being indirectly coupled.

Terms such as "top," "bottom," "front," "rear" and the like if used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Various items may be arranged differently (e.g., arranged in a different order, or partitioned in a different way) all without departing from the scope of the subject technology. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A connector comprising:
   a first connector portion comprising:
      a connector housing comprising a connector body defining a housing volume, a luer opening and a valve opening, wherein the housing volume is in fluid communication with the luer opening and the valve opening;
      a luer portion comprising a luer end and a housing end, the luer portion defining a lumen extending between the luer end and the housing end, wherein the housing end of the luer portion extends through the luer opening of the connector body to couple the luer portion to the connector housing and the lumen is in fluid communication with the housing volume; and
      a deformable valve member disposed within the housing volume and comprising a spherical portion extending partially through the valve opening, wherein the spherical portion defines a slit, and the deformable valve member is configured to selectively prevent fluid flow from the housing volume through the valve opening and to deform to expand the slit and permit fluid flow from the housing volume through the valve opening; and
   a second connector portion comprising:
      a second connector housing comprising a second connector body defining a second housing volume, a tubing opening and a second valve opening, wherein the second housing volume is in fluid communication with the tubing opening and the second valve opening; and
      a second deformable valve member disposed within the second housing volume and extending partially through the second valve opening, and
      wherein the deformable valve member and the second deformable valve member are configured to selectively prevent fluid flow through the respective housing volume and the second housing volume when the first and second connector portions are spaced apart and to deform to permit fluid flow between the first and second connector portions when the first and second connector portions are coupled and the deformable valve member and the second deformable valve member are in contact.

2. The connector of claim 1, wherein the deformable valve member comprises an elastomeric material.

3. The connector of claim 1, wherein the spherical portion of the deformable valve member comprises a hemispherical shape.

4. The connector of claim 1, wherein the connector body comprises a planar connector surface and the valve opening is defined through the planar connector surface.

5. The connector of claim 1, wherein the luer opening and the valve opening are equal in diameter.

6. The connector of claim 1, wherein the connector body comprises a collar extending axially beyond the spherical portion of the deformable valve member.

7. The connector of claim 1, wherein the luer portion is releasably coupled to the connector housing.

8. The connector of claim 1, wherein the connector housing and the luer portion retain the deformable valve member within the housing volume.

9. The connector of claim 1
   wherein the connector portion and the second connector portion are configured to be releasably coupled.

10. The connector of claim 9, wherein the connector housing further comprises an engagement lip extending radially from the connector body, and the second connector housing comprises an engagement groove disposed around the second connector body, and the engagement lip is configured to releasably engage the engagement groove.

11. The connector of claim 9, wherein the first and second connector portion are configured to separate with about 5 pounds of force.

12. The connector of claim 1, wherein the second deformable valve member comprises a second spherical portion extending partially through the second valve opening.

13. The connector of claim 12, wherein the second spherical portion defines a second slit.

14. The connector of claim 13, wherein the deformable valve member and the second deformable valve member are configured to selectively deform to expand the slit and the second slit and permit fluid flow between the first and second connector portions when the first and second connector portions are coupled and the deformable valve member and the second deformable valve member are in contact.

* * * * *